United States Patent
Altenburger et al.

(10) Patent No.: US 8,466,292 B2
(45) Date of Patent: Jun. 18, 2013

(54) 5,6-BISARYL-2-PYRIDINE-CARBOXAMIDE DERIVATIVES, PREPARATION THEREOF AND THERAPEUTIC APPLICATION THEREOF AS UROTENSIN II RECEPTOR ANTAGONISTS

(75) Inventors: Jean-Michel Altenburger, Paris (FR); Valérie Fossey, Paris (FR); Daniel Galtier, Paris (FR); Frédéric Petit, Paris (FR)

(73) Assignee: Sanofi, Paris (FR)

( * ) Notice: Subject to any disclaimer, the term of this patent is extended or adjusted under 35 U.S.C. 154(b) by 238 days.

(21) Appl. No.: 12/851,941

(22) Filed: Aug. 6, 2010

(65) Prior Publication Data

US 2011/0009426 A1    Jan. 13, 2011

Related U.S. Application Data

(63) Continuation of application No. PCT/FR2009/000128, filed on Feb. 5, 2009.

(30) Foreign Application Priority Data

Feb. 7, 2008 (FR) .................................... 08 00651

(51) Int. Cl.
  *C07D 211/70* (2006.01)
  *C07D 211/72* (2006.01)
  *A61K 31/44* (2006.01)

(52) U.S. Cl.
  USPC ........................... 546/316; 546/328; 514/334

(58) Field of Classification Search
  None
  See application file for complete search history.

(56) References Cited

FOREIGN PATENT DOCUMENTS

| FR | 2856684 A1 | 12/2004 |
|---|---|---|
| WO | WO03/051850 A1 | 6/2003 |
| WO | WO2004/073634 A2 | 9/2004 |
| WO | WO2004/078114 A2 | 9/2004 |
| WO | WO2008/020124 A1 | 2/2008 |

OTHER PUBLICATIONS

Watanabe, Takuya et al., "Synergistic Effect of Urotensin II with Mildly Oxidized LDL on DNA Synthesis in Vascular Smooth Muscle Cells," Circulation (2001), vol. 104, pp. 16-18.
Tzanidis, Alex et al., "Direct Actions of Urotensin II on the Hear: Implications for Cardiac Fibrosis and Hypertrophy," Circulation Research (2003), vol. 93, pp. 246-253.
Takahashi, Kazuhiro et al., "Expression of urotensin II and its receptor in adrenal tumors and stimulation of proliferation of cultured tumor cells by urotensin II," Peptides (2003), vol. 24, pp. 301-306.
Richards, A. Mark et al., "Urotensin II in the cardiovascular system," Peptides (2004), vol. 25, pp. 1795-1802.
Matsumoto, Yoshio et al., "Intracerebroventricular administration of urotensin II promotes anxiogenic-like behaviors in rodents," Neuroscience Letters (2004), vol. 358, pp. 99-102.
Evans, David A. et al., "A General Method for the Synthesis of Enantiomerically Pure B-Substituted, S-Amino Acids through a-Substituted Succinic Acid Derivatives," Journal of Organic Chemistry (1999), vol. 64, pp. 6411-6417.
Kelly, T. Ross et al., "Total Synthesis of Dimethyl Sulfomycinamate," Journal of Organic Chemistry (1996), vol. 61, pp. 4623-4633.
Avenoza, Aberto et al., "Synthesis of 1-amino-4-hydroxycyclohexane-1-carboxylic Acids," Journal of the Chemical Society, Perkin Transactions 1 (1999), pp. 3375-3379.
Douglas, Stephen A. et al., "Differential vasoconstrictor activity of human urotensin-II vascular tissue isolated from the rat, mouse, dog, pig, marmoset and cynomolgus monkey," British Journal of Pharmacology, (2000), vol. 131, pp. 1262-1274.
Doggrell, Sheila A., "Urotensin-II and the cardiovascular system—the importance of developing modulators," Expert Opinion on Investigational Drugs (2004), vol. 13, No. 5, pp. 479-487.
Ames, Robert S. et al., "Human urotensin-II is a potent vasocontrictor and agonist for the orphan receptor GPR14," Nature, (1999), vol. 401, pp. 282-286.
International Search Report dated Aug. 28, 2009 issued in PCT/FR2009/000128.
French Search Report dated Jun. 4, 2008 issued in FR0800651.

*Primary Examiner* — Janet Andres
*Assistant Examiner* — Heidi Reese
(74) *Attorney, Agent, or Firm* — Scully, Scott, Murphy & Presser, P.C.

(57) ABSTRACT

The present invention is directed to compounds of the general formula:

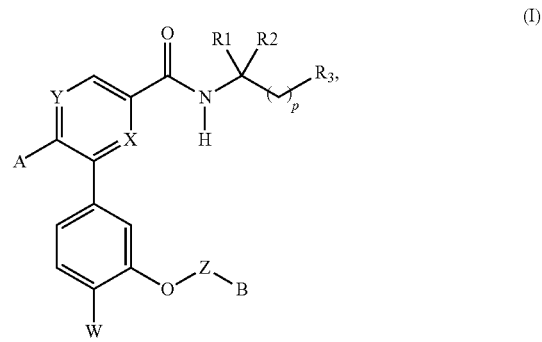

(I)

as well as pharmaceutical compositions thereof. The invention is also directed to their therapeutic use as urotensin II receptor antagonists, e.g., in the treatment of cardiac, coronary, and central nervous system disorders. In particular embodiments, the invention relates to 5,6-bisaryl-2-pyridinecarboxamides, to their preparation and to their therapeutic use as urotensin II receptor antagonists.

9 Claims, No Drawings

5,6-BISARYL-2-PYRIDINE-CARBOXAMIDE DERIVATIVES, PREPARATION THEREOF AND THERAPEUTIC APPLICATION THEREOF AS UROTENSIN II RECEPTOR ANTAGONISTS

The present invention relates to 5,6-bisaryl-2-pyridinecarboxamides, to their preparation and to their therapeutic use as urotensin II receptor antagonists.

Urotensin II is a cyclic peptide formed from 11 amino acids and considered as being one of the most powerful vasoconstrictors known to date (Ames et al., 1999, Nature 401, 282-286). Its biological activity is mediated via the activation of a 7-domain transmembrane receptor coupled to the G proteins, GPR14, known as UT (Urotensin II Receptor) by the International Union of Basic and Clinical Pharmacology (IUPHAR). Activation of the urotensin II receptor gives rise to mobilization of the intracellular calcium. Urotensin II and its receptor are highly expressed in the cardiovascular system, but also at the renal and cerebral level and in the endocrine system (Richards and Charles, 2004, Peptides 25, 1795-1802). On isolated vessels, human urotensin II causes vasoconstriction whose intensity varies as a function of the territory and of the species concerned (Douglas et al., 2000, Br. J. Phamacol. 131, 1262-1274). The administration of urotensin II to anesthetized primates induces an increase in peripheral vascular resistance and degradation of cardiac contractility and of the heart rate, which may lead at high doses to cardiovascular collapse and ultimately the death of the animal (Ames et al., 1999, Nature 401, 282-286). Moreover, urotensin II stimulates the proliferation of vascular smooth muscle cells and acts in synergy with the mitogenic activity of serotonin and of oxidized LDLs (Low Density Lipoproteins) (Watanabe et al., 2001, Circulation 104; 16-18). On cardiomyocytes in culture, urotensin II induces cellular hypertrophy and an increase in the synthesis of extracellular matrix (Tzanidis A., et al., 2003, Circ. Res. 93, 246-253).

The plasmatic and urinary levels of urotensin II were reported to be increased in a certain number of cardiovascular, renal and metabolic pathologies in man. These pathologies include arterial hypertension, cardiac insufficiency, renal insufficiency, diabetes and liver cirrhosis (Richards and Charles, 2004, Peptides 25, 1795-1802; Doggrell, 2004, Expert Opin Investig Drugs 13, 479-487).

Central effects of urotensin II have also been described (Matsumoto Y., et al., Neurosci. Lett., 2004, 358, 99).

Finally, it has been shown that certain tumor cell lines overexpress the urotensin II receptor (Takahashi K., et al., Peptides, 2003, 24, 301).

Urotensin II receptor antagonists may be useful for treating congestive cardiac insufficiency, cardiac ischemia, myocardial infarction, cardiac hypertrophy and fibrosis, coronary diseases and atherosclerosis, systemic and pulmonary arterial hypertension, portal hypertension and hepatic fibrosis, post-angioplasty restenosis, acute and chronic renal insufficiency of diabetic and/or hypertensive origin, diabetes, vascular inflammation, and aneurisms. Moreover, urotensin II receptor antagonists may be useful for treating central nervous system disorders, including neurodegenerative diseases, strokes, stress, anxiety, aggressiveness, depression, schizophrenia, vomiting and sleep disorders. Finally, urotensin II receptor antagonists may also be useful for treating certain cancers.

The compounds according to the present invention correspond to formula (I):

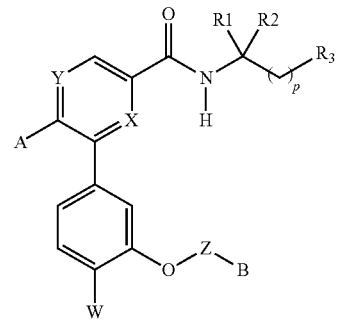

in which:
X and Y represent, independently of each other, a nitrogen atom or a chain —CR4-, in which R4 represents a hydrogen atom or a (C1-C4) alkyl or alkoxy group;
A represents an aryl or heteroaryl group, said aryl or heteroaryl groups being optionally substituted with one or more groups chosen from a halogen atom, a hydroxyl group, (C1-C4) alkyl, (C3-C5) cycloalkyl, (C1-C4) alkoxy optionally substituted with a (C1-C4) alkoxy, haloalkyl or haloalkoxy group, or a nitrile group;
W represents a halogen atom or a haloalkyl group;
Z represents a (C1-C4) alkylene group optionally substituted with one or more groups chosen from a halogen atom and (C1-C4) alkyl, hydroxyl and (C1-C4) alkoxy groups;
B represents a group —NR4R5, in which R4 and R5 represent, independently of each other, a (C1-C4) alkyl group;
R1 and R2 represent:
either, R1 represents a hydrogen atom and R2 represents a (C1-C4) alkyl group,
or R1 and R2 form, together with the carbon atom to which they are attached, a monocyclic or polycyclic system chosen from: a (C3-C8) cycloalkyl group, a bridged bicyclic group or a bridged tetracyclic group, said system possibly being substituted with one or more hydroxyl groups;
R3 represents:
either a group C(O)R5 with R5 representing a (C1-C4) alkoxy group optionally substituted with a (C1-C4) alkoxy group or a group NR6R7 with R6 and R7, independently of each other, representing a hydrogen atom or a (C1-C4) alkyl, (C3-C5) cycloalkyl, (C1-C4) alkylsulfonyl or haloalkyl group,
or a group CH$_2$XR8 in which:
X represents an oxygen atom and R8 represents a hydrogen atom or a (C1-C4) alkyl group,
or X represents an NH group and R8 represents a (C1-C4) alkylcarbonyl, (C1-C4) alkylcarboxyl or (C1-C4) alkylsulfonyl group,
or a nitrile group (CN);
p represents an integer equal to 0 or 1.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or salified with acids or bases, especially pharmaceutically acceptable acids or bases. Such addition salts form part of the invention.

These salts are advantageously prepared with pharmaceutically acceptable acids, but the salts of other acids that are useful, for example, for purifying or isolating the compounds of formula (I) also form part of the invention.

The compounds of formula (I) may also exist in the form of hydrates or solvates, i.e. in the form of associations or combinations with one or more water or solvent molecules. Such hydrates and solvates also form part of the invention.

Among the compounds described in the present invention, mention may be made of a first group of compounds corresponding to formula (I) in which:

- X and Y represent, independently of each other, a nitrogen atom or a chain —CR4-, in which R4 represents a hydrogen atom;
- A represents an aryl or heteroaryl group, said aryl and heteroaryl groups being optionally substituted with one or more groups chosen from a halogen atom, a hydroxyl group, (C1-C4) alkyl, (C3-C5) cycloalkyl, (C1-C4) alkoxy optionally substituted with a (C1-C4) alkoxy, haloalkyl or haloalkoxy group;
- W represents a halogen atom;
- Z represents a (C1-C4) alkylene group;
- B represents a group —NR4R5, in which R4 and R5 represent, independently of each other, a (C1-C4) alkyl group,
- R1 and R2 represent:
- either, R1 represents a hydrogen atom and R2 represents a (C1-C4) alkyl group,
- or R1 and R2 form, together with the carbon atom to which they are attached, a monocyclic or polycyclic system chosen from: a (C3-C8) cycloalkyl group or a bridged tetracyclic group, said system possibly being substituted with one or more hydroxyl groups;
- R3 represents:
- either a group C(O)R5 with R5 representing a (C1-C4) alkoxy group optionally substituted with a (C1-C4) alkoxy group or a group NR6R7 with R6 and R7, independently of each other, representing a hydrogen atom or a (C1-C4) alkyl, (C3-C5) cycloalkyl, (C1-C4) alkylsulfonyl or haloalkyl group,
- or a group $CH_2XR8$ with X representing an oxygen atom and R8 representing a hydrogen atom or a (C1-C4) alkyl group,
- or a nitrile group (CN);
- p represents an integer equal to 0 or 1.

Among the compounds of formula (I) that are subjects of the invention, mention may be made of a second group of compounds that is defined as follows:

- X and Y represent, independently of each other, a nitrogen atom or a chain —CR4-, in which R4 represents a hydrogen atom;
- and/or
- A represents an aryl or heteroaryl group, said aryl or heteroaryl groups being optionally substituted with one or more groups chosen from a halogen atom, a hydroxyl group, (C1-C4) alkyl, (C3-C5) cycloalkyl, (C1-C4) alkoxy optionally substituted with a (C1-C4) alkoxy, haloalkyl or haloalkoxy group;
- and/or
- W represents a halogen atom;
- and/or
- Z represents a (C1-C4) alkylene group;
- and/or
- B represents a group —NR4R5, in which R4 and R5 represent, independently of each other, a (C1-C4) alkyl group,
- and/or
- R1 and R2 represent:
- either, R1 represents a hydrogen atom and R2 represents a (C1-C4) alkyl group,
- or R1 and R2 form, together with the carbon atom to which they are attached, a monocyclic or polycyclic system chosen from: a (C3-C8) cycloalkyl group or a bridged tetracyclic group, said system possibly being substituted with one or more hydroxyl groups;
- and/or
- R3 represents:
- either a group C(O)R5 with R5 representing a (C1-C4) alkoxy group optionally substituted with a (C1-C4) alkoxy group or a group NR6R7 with R6 and R7, independently of each other, representing a hydrogen atom or a (C1-C4) alkyl, (C3-C5) cycloalkyl, (C1-C4) alkylsulfonyl or haloalkyl group,
- or a group $CH_2XR8$ with X representing an oxygen atom and R8 representing a hydrogen atom or (C1-C4) alkyl group,
- and/or
- p represents an integer equal to 0 or 1.

Among the compounds of formula (I) that are subjects of the invention, mention may be made of a third group of compounds that is defined as follows:

- X and Y represent, independently of each other, a nitrogen atom or a chain —CR4-, in which R4 represents a hydrogen atom;
- and/or
- A represents an aryl or heteroaryl group, said aryl or heteroaryl groups being optionally substituted with one or more groups chosen from a halogen atom, a hydroxyl group, (C1-C4) alkyl, (C3-C5) cycloalkyl, (C1-C4) alkoxy optionally substituted with a (C1-C4) alkoxy, haloalkyl or haloalkoxy group;
- and/or
- W represents a halogen atom;
- and/or
- Z represents a (C1-C4) alkylene group;
- and/or
- B represents a group —NR4R5, in which R4 and R5 represent, independently of each other, a (C1-C4) alkyl group,
- and/or
- R1 and R2 represent:
- either, R1 represents a hydrogen atom and R2 represents a (C1-C4) alkyl group,
- or R1 and R2 form, together with the carbon atom to which they are attached, a monocyclic or polycyclic system chosen from: a (C3-C8) cycloalkyl group or a bridged tetracyclic group, said system possibly being substituted with one or more hydroxyl groups;
- and/or
- R3 represents:
- either a group C(O)R5 with R5 representing a (C1-C4) alkoxy group optionally substituted with a (C1-C4) alkoxy group or a group NR6R7 with R6 and R7, independently of each other, representing a hydrogen atom or a (C1-C4) alkyl, (C3-C5) cycloalkyl, (C1-C4) alkylsulfonyl or haloalkyl group,
- or a group $CH_2XR8$ with X representing an oxygen atom and R8 representing a hydrogen atom or a (C1-C4) alkyl group,
- or a nitrile group (CN);
- and/or
- p represents an integer equal to 0 or 1.

Among the compounds of formula (I) that are subjects of the invention, mention may be made of a fourth group of compounds for which X and Y represent, independently of each other, a nitrogen atom or a chain —CR4-, in which R4 represents a hydrogen atom.

Among the compounds of formula (I) that are subjects of the invention, mention may be made of a fifth group of compounds for which A represents an aryl or heteroaryl group, said aryl or heteroaryl groups being optionally substituted with one or more groups chosen from a halogen atom, a hydroxyl group, (C1-C4) alkyl, (C3-C5) cycloalkyl, (C1-C4) alkoxy optionally substituted with a (C1-C4) alkoxy, haloalkyl or haloalkoxy group.

The aryl and heteroaryl groups of the fifth group may be chosen from a phenyl, piperonyl, pyridinyl or pyrazolyl group optionally linked to the central nucleus comprising X and Y via a nitrogen atom.

Among the compounds of formula (I) that are subjects of the invention, mention may be made of a sixth group of compounds for which W represents a halogen atom.

Among the compounds of formula (I) that are subjects of the invention, mention may be made of a seventh group of compounds for which Z represents a (C1-C4) alkylene group.

Among the compounds of formula (I) that are subjects of the invention, mention may be made of an eighth group of compounds for which B represents a group —NR4R5, in which R4 and R5 represent, independently of each other, a (C1-C4) alkyl group.

Among the compounds of formula (I) that are subjects of the invention, mention may be made of a ninth group of compounds for which R1 represents a hydrogen atom and R2 represents a (C1-C4) alkyl group.

Among the compounds of formula (I) that are subjects of the invention, mention may be made of a tenth group of compounds for which R1 and R2 form, together with the carbon atom to which they are attached, a monocyclic or polycyclic system chosen from: a (C3-C8) cycloalkyl group or a bridged tetracyclic group, said system possibly being substituted with one or more hydroxyl groups.

Said bridged tetracyclic group of the tenth group may be an adamantyl group.

Among the compounds of formula (I) that are subjects of the invention, mention may be made of an eleventh group of compounds for which R3 represents a group C(O)R5 with R5 representing a (C1-C4) alkoxy group optionally substituted with a (C1-C4) alkoxy group or a group NR6R7 with R6 and R7, independently of each other, representing a hydrogen atom or a (C1-C4) alkyl, (C3-C5) cycloalkyl, (C1-C4) alkylsulfonyl or haloalkyl group.

Among the compounds of formula (I) that are subjects of the invention, mention may be made of a twelfth group of compounds for which R3 represents a group —CH$_2$XR8 with X representing an oxygen atom and R8 representing a hydrogen atom or a (C1-C4) alkyl group.

Among the compounds of formula (I) that are subjects of the invention, mention may be made of a thirteenth group of compounds for which p represents an integer equal to 0.

Among the compounds of formula (I) that are subjects of the invention, mention may be made of a fourteenth group of compounds for which p represents an integer equal to 1.

All the groups or subgroups may be used independently of each other in combination to obtain compounds according to the invention.

Among the combinations of groups corresponding to compounds that are subjects of the invention, mention may be made of a first combination corresponding to compounds for which:

X represents a nitrogen atom and Y represents a nitrogen atom or a chain —CR4-, in which R4 represents a hydrogen atom;

A represents an aryl group optionally substituted with one or more groups chosen from a halogen atom, (C1-C4) alkyl, (C3-C5) cycloalkyl, (C1-C4) alkoxy and haloalkoxy, or represents a heteroaryl group optionally substituted with one or more groups chosen from a halogen atom and (C1-C4) alkyl;

W represents a halogen atom,

Z represents a (C1-C4) alkylene group;

B represents a group —NR4R5, in which R4 and R5 represent, independently of each other, a (C1-C4) alkyl group, R1 and R2 represent:

either, R1 represents a hydrogen atom and R2 represents a (C1-C4) alkyl group, or R1 and R2 form, together with the carbon atom to which they are attached, a (C3-C8) cycloalkyl group optionally substituted with one or more hydroxyl groups or an adamantyl group;

R3 represents:

either a group C(O)R5 with R5 representing a (C1-C4) alkoxy group optionally substituted with a (C1-C4) alkoxy group or a group NR6R7 with R6 representing a hydrogen atom and R7 representing a (C1-C4) alkyl, (C3-C5) cycloalkyl, (C1-C4) alkylsulfonyl or haloalkyl group, or a group CH$_2$XR8 with X representing an oxygen atom and R8 representing a hydrogen atom or a (C1-C4) alkyl group;

p represents an integer equal to 0 or 1.

Among the combinations of groups corresponding to compounds that are subjects of the invention, mention may be made of a second combination corresponding to compounds for which:

X represents a nitrogen atom and Y represents a nitrogen atom or a chain —CR4-, in which R4 represents a hydrogen atom;

A represents an aryl group optionally substituted with one or more groups chosen from a halogen atom, a (C1-C4) alkyl group or a (C1-C4) alkoxy group or represents a heteroaryl group optionally substituted with one or more halogen atoms or one or more (C1-C4) alkyl groups, W represents a halogen atom, Z represents a (C1-C4) alkylene group;

B represents a group —NR4R5, in which R4 and R5 represent, independently of each other, a (C1-C4) alkyl group, R1 and R2 represent:

either, R1 represents a hydrogen atom and R2 represents a (C1-C4) alkyl group, or R1 and R2 form, together with the carbon atom to which they are attached, a (C3-C8) cycloalkyl group or an adamantyl group;

R3 represents:

either a group C(O)R5 with R5 representing a (C1-C4) alkoxy group optionally substituted with a (C1-C4) alkoxy group or a group NR6R7 with R6 representing a hydrogen atom and R7 representing a hydrogen atom or a (C1-C4) alkyl, (C3-C5) cycloalkyl or (C1-C4) alkylsulfonyl group, or a group —CH$_2$XR8 with X representing an oxygen atom and R8 representing a hydrogen atom;

p represents an integer equal to 0 or 1.

Among the combinations of groups corresponding to compounds that are subjects of the invention, mention may be made of a third combination corresponding to compounds for which:

X represents a nitrogen atom and Y represents a chain —CR4-, in which R4 represents a hydrogen atom;

A represents an aryl group optionally substituted with one or more groups chosen from a halogen atom, (C1-C4) alkyl and (C1-C4) alkoxy or represents a heteroaryl group optionally substituted with one or more halogen atoms;

W represents a halogen atom,

Z represents a (C1-C4) alkylene group;

B represents a group —NR4R5, in which R4 and R5 represent, independently of each other, a (C1-C4) alkyl group, R1 and R2 represent:
either, R1 represents a hydrogen atom and R2 represents a (C1-C4) alkyl group, the carbon atom that bears R1 and R2 being of (S) absolute configuration,
or R1 and R2 form, together with the carbon atom to which they are attached, a (C3-C8) cycloalkyl group;

R3 represents:
either a group C(O)R5 with R5 representing a (C1-C4) alkoxy group optionally substituted with a (C1-C4) alkoxy group or a group NR6R7 with R6 representing a hydrogen atom and R7 representing a hydrogen atom or a (C1-C4) alkyl, (C3-C5) cycloalkyl, (C1-C4) alkylsulfonyl or haloalkyl group,
or a group —CH$_2$XR8 with X representing an oxygen atom and R8 representing a hydrogen atom or a (C1-C4) alkyl group;

p represents an integer equal to 1.

In the context of the present invention, and unless otherwise mentioned in the text, the following definitions apply:

a halogen atom: a fluorine, chlorine, bromine or iodine atom;

an alkyl group: a saturated aliphatic group which is linear, comprising from 1 to 5 carbon atoms, or, when the alkyl chain comprises at least three carbon atoms, which may be linear, branched or partially cyclized. Examples that may be mentioned include methyl, ethyl, propyl, isopropyl, butyl, isobutyl, tert-butyl, pentyl and methylenecyclopropyl groups;

an alkylene group: an alkyl group as defined above, which is divalent. Examples that may be mentioned include methylene, propylene, butylene, ethylene (—CH$_2$—CH$_2$—) or 2-methylpropylene groups;

a cycloalkyl group: a saturated cyclic group, which comprises from 3 to 8 carbon atoms and which is cyclic. Examples that may be mentioned include cyclopropyl, cyclopentyl and cyclohexyl groups;

a bridged polycyclic group: a polycyclic system comprising two to four saturated rings of 7 to 10 carbon atoms, adjacent carbons of which are connected together and simultaneously belong to at least two rings, for example a bridged bicyclic group or a bridged tetracyclic group such as the adamantyl group;

an aryl group: a monocyclic aromatic group comprising 5 or 6 carbon atoms, for example a phenyl group, this ring possibly being fused with a partially saturated heterocyclic group comprising 5 or 6 atoms, including one or two heteroatoms such as an oxygen atom, for example a dioxolyl group to form a piperonyl group;

a heteroaryl group: a cyclic aromatic group comprising 5 or 6 atoms including one or more heteroatoms such as a nitrogen atom. Examples of heteroaryl groups that may be mentioned include pyridinyl and pyrazolyl groups;

a cycloalkylene group: a cycloalkyl group as defined above, which is divalent;

a haloalkyl group: an alkyl group as defined above, one or more hydrogen atoms of which have been replaced with a halogen atom. Examples that may be mentioned include trifluoromethyl and difluoromethyl groups;

a haloalkoxy group: a group of formula —O-haloalkyl in which the haloalkyl group is as defined above. An example that may be mentioned is the group —O—CHF$_2$;

an alkoxy group: a group of formula —O-alkyl in which the alkyl group is as defined previously.

Among the compounds that are subjects of the invention, mention may be made especially of the following compounds:

1. methyl 1-{[(3,5-dichloro-2'-{4-chloro-3-[3-(dimethylamino)propoxy]-]-phenyl}-2,3'-bipyridin-6'-yl)carbonyl]amino}cyclohexanecarboxylate;
2. methyl 1-({[6-{4-chloro-3-[3-(dimethylamino)propoxy]phenyl}-5-(4-hydroxy-2-methylphenyl)pyridin-2-yl]carbonyl}amino)cyclohexane-carboxylate;
3. methyl 1-({[6-{4-chloro-3-[3-(dimethylamino)propoxy]phenyl}-5-(5-hydroxy-2-methylphenyl)pyridin-2-yl]carbonyl}amino)cyclohexane-carboxylate;
4. methyl 1-({[6-{4-chloro-3-[3-(dimethylamino)propoxy]phenyl}-5-(2-methylphenyl)pyridin-2-yl]carbonyl}amino)cyclohexane-carboxylate;
5. methyl 1-{[(3-chloro-2'-{4-chloro-3-[3-(dimethylamino)propoxy]-]-phenyl}-5-methyl-2,3'-bipyridin-6'-yl)carbonyl]amino}cyclohexane-carboxylate;
6. methyl 1-{[(6-{4-chloro-3-[3-(dimethylamino)propoxy]phenyl}-5-[5-(2-methoxyethoxy)-2-methylphenyl]pyridin-2-yl)carbonyl]amino}cyclo-hexanecarboxylate;
7. methyl 1-({[6-{4-chloro-3-[3-(dimethylamino)propoxy]phenyl}-5-(5-cyclopropyl-2-methylphenyl)pyridin-2-yl]carbonyl}amino)cyclo-hexanecarboxylate;
8. methyl 1-({[6-{4-chloro-3-[3-(dimethylamino)propoxy]phenyl}-5-(5-isopropoxy-2-methylphenyl)pyridin-2-yl]carbonyl}amino)cyclo-hexane-carboxylate;
9. methyl 1-({[6-{4-chloro-3-[3-(dimethylamino)propoxy]phenyl}-5-(2-chloro-5-propoxyphenyl)pyridin-2-yl]carbonyl}amino)cyclohexane-carboxylate;
10. methyl 1-({[6-{4-chloro-3-[3-(dimethylamino)propoxy]phenyl}-5-(5-ethoxy-2-methylphenyl)pyridin-2-yl]carbonyl}amino)cyclohexane-carboxylate;
11. methyl 1-({[6-{4-chloro-3-[3-(dimethylamino)propoxy]phenyl}-5-(6-methyl-1,3-benzodioxol-5-yl)pyridin-2-yl]carbonyl}amino)cyclo-hexanecarboxylate;
12. methyl 1-{[(3-chloro-2'-{4-chloro-3-[3-(dimethylamino)propoxy]-]-phenyl}-5-fluoro-2,3'-bipyridin-6'-yl)carbonyl]amino}cyclohexane-carboxylate;
13. methyl 1-{[(2'-{4-chloro-3-[3-(dimethylamino)propoxy]phenyl}-3,5-dimethyl-2,3'-bipyridin-6'-yl)carbonyl]amino}cyclohexanecarboxylate;
14. methyl 1-({[6-{4-chloro-3-[3-(dimethylamino)propoxy]phenyl}-5-(3-hydroxy-2-methylphenyl)pyridin-2-yl]carbonyl}amino)cyclohexane-carboxylate;
15. methyl 1-{[(2-{4-chloro-3-[3-(dimethylamino)propoxy]phenyl}-2'-methyl-3,3'-bipyridin-6-yl)carbonyl]amino}cyclohexanecarboxylate;
16. methyl 1-{[(6-{4-chloro-3-[3-(dimethylamino)propoxy]phenyl}-5-[5-(difluoromethoxy)-2-methylphenyl]pyridin-2-yl)carbonyl]amino}-cyclohexanecarboxylate;

17. methyl 1-{[(6-{4-chloro-3-[3-(dimethylamino)propoxy]phenyl}-5-[2-(difluoromethyl)-5-methylphenyl]pyridin-2-yl)carbonyl]amino}cyclo-hexanecarboxylate;
18. methyl 1-({[6-{4-chloro-3-[3-(dimethylamino)propoxy]phenyl}-5-(3,5-dimethyl-1H-pyrazol-1-yl)pyridin-2-yl]carbonyl}amino)cyclohexane-carboxylate;
19. methyl 1-({[6-{4-chloro-3-[3-(dimethylamino)propoxy]phenyl}5-(3,5-diethyl-1H-pyrazol-1-yl)pyridin-2-yl]carbonyl}amino)cyclohexane-carboxylate;
20. methyl 1-({[6-{4-chloro-3-[3-(dimethylamino)propoxy]phenyl}-5-(2,4-dimethylphenyl)pyrazin-2-yl]carbonyl}amino)cyclohexane-carboxylate;
21. methyl 1-({[6-{4-chloro-3-[3-(dimethylamino)propoxy]phenyl}-5-(2-chloro-5-ethoxyphenyl)pyrazin-2-yl]carbonyl}amino)cyclohexane-carboxylate;
22. methyl(3S)-3-({[6-{4-chloro-3-[3-(dimethylamino)propoxy]phenyl}-5-(2-chloro-5-methylphenyl)pyridin-2-yl]carbonyl}amino)-4-methyl-pentanoate;
23. methyl(3S)-3-({[6-{4-chloro-3-[3-(dimethylamino)propoxy]phenyl}-5-(2,4-dimethylphenyl)pyridin-2-yl]carbonyl}amino)-4,4-dimethyl-pentanoate;
24. methyl(3S)-3-({[6-{4-chloro-3-[3-(dimethylamino)propoxy]phenyl}-5-(2-chloro-5-ethoxyphenyl)pyrazin-2-yl]carbonyl}amino)-4,4-dimethyl-pentanoate;
25. methyl(3S)-3-{[(3-chloro-2'-{4-chloro-3-[3-(dimethylamino)propoxy]-]-phenyl}-5-fluoro-2,3'-bipyridin-6'-yl)carbonyl]amino}-4,4-dimethyl-pentanoate;
26. methyl 2-({[6-{4-chloro-3-[3-(dimethylamino)propoxy]phenyl}-5-(2-chlorophenyl)pyridin-2-yl]carbonyl}amino)adamantane-2-carboxylate;
27. 2-methoxyethyl(3S)-3-({[6-{4-chloro-3-[3-(dimethylamino)propoxy]-]-phenyl}-5-(2-methylphenyl)pyridin-2-yl]carbonyl}amino)-4,4-dimethyl-pentanoate;
28. methyl(3S)-3-({[6-{4-chloro-3-[3-(dimethylamino)propoxy]phenyl}-5-(2-methylphenyl)pyridin-2-yl]carbonyl}amino)-4,4-dimethylpentanoate;
29. ethyl(3S)-3-({[6-{4-chloro-3-[3-(dimethylamino)propoxy]phenyl}-5-(2-methylphenyl)pyridin-2-yl]carbonyl}amino)-4,4-dimethylpentanoate;
30. isopropyl(3S)-3-({[6-{4-chloro-3-[3-(dimethylamino)propoxy]-phenyl}-5-(2-methylphenyl)pyridin-2-yl]carbonyl}amino)-4,4-dimethyl-pentanoate;
31. methyl(3S)-3-({[6-{4-chloro-3-[3-(dimethylamino)propoxy]phenyl}-5-(2-chlorophenyl)pyridin-2-yl]carbonyl}amino)-4,4-dimethyl-pentanoate;
32. N-[(1S)-1-(2-amino-2-oxoethyl)-2,2-dimethylpropyl]-6-{4-chloro-3-[3-(dimethylamino)propoxy]phenyl}-5-(2-methylphenyl)pyridine-2-carboxamide;
33. 6-{4-chloro-3-[3-(dimethylamino)propoxy]phenyl}-N-{(1S)-2,2-dimethyl-1-[2-(methylamino)-2-oxoethyl]propyl}-5-(2-methylphenyl)pyridine-2-carboxamide;
34. 6-{4-chloro-3-[3-(dimethylamino)propoxy]phenyl}-N-[(1S)-2,2-dimethyl-1-{2-[(methylsulfonyl)amino]-2-oxoethyl}propyl]-5-(2-methylphenyl)pyridine-2-carboxamide;
35. 6-{4-chloro-3-[3-(dimethylamino)propoxy]phenyl}-N-[(1S)-1-{2-[(1,1,1-trifluoroethyl)amino]-2-oxoethyl}-2,2-dimethylpropyl]-5-(2-methylphenyl)pyridine-2-carboxamide;
36. 6-{4-chloro-3-[3-(dimethylamino)propoxy]phenyl}-N-[(1S)-1-{2-[cyclo-propyl(methyl)amino]-2-oxoethyl}-2,2-dimethylpropyl]-5-(2-methyl-phenyl)pyridine-2-carboxamide;
37. 6-{4-chloro-3-[3-(dimethylamino)propoxy]phenyl}-N-[(1S)-1-(2-hydroxyethyl)-2,2-dimethylpropyl]-5-(2-methylphenyl)pyridine-2-carboxamide;
38. 6-{4-chloro-3-[3-(dimethylamino)propoxy]phenyl}-N-[(1S)-1-(2-methoxyethyl)-2,2-dimethylpropyl]-5-(2-methylphenyl)pyridine-2-carboxamide;
39. 6-{4-chloro-3-[3-(dimethylamino)propoxy]phenyl}-N-[(2S)-1-cyano-3,3-dimethylbutan-2-yl]-5-(2-methylphenyl)pyridine-2-carboxamide;
40. methyl cis-1-{[(3,5-dichloro-2'-{4-chloro-3-[3-(dimethylamino)propoxy]phenyl}-2,3'-bipyridin-6'-yl)carbonyl]amino}-4-hydroxycyclo-hexanecarboxylate;
41. methyl cis-1-({[6-{4-chloro-3-[3-(dimethylamino)propoxy]phenyl}-5-(2,4-dimethylphenyl)pyridin-2-yl]carbonyl}amino)-4-hydroxycyclo-hexanecarboxylate;
42. methyl cis-1-({[6-{4-chloro-3-[3-(dimethylamino)propoxy]phenyl}-5-(2-methylphenyl)pyridin-2-yl]carbonyl}amino)-4-hydroxycyclo-hexanecarboxylate;
43. methyl cis-1-({[6-{4-chloro-3-[3-(dimethylamino)propoxy]phenyl}-5-(5-ethoxy-2-methylphenyl)pyridin-2-yl]carbonyl}amino)-4-hydroxy-cyclohexanecarboxylate;
44. methyl cis-1-{[(3-chloro-2'-{4-chloro-3-[3-(dimethylamino)propoxy]-phenyl}-5-methyl-2,3'-bipyridin-6'-yl)carbonyl]amino}-4-hydroxy-cyclohexanecarboxylate.

It should be noted that the above compounds have been named according to the IUPAC nomenclature using the ACD/Name software, version 10.0, Advanced Chemistry Development, Inc.: Toronto ON, Canada, www.acdlabs.com, 2006.

In the text hereinbelow, the term "protective group" (PG) means a group that firstly allows a reactive function such as a hydroxyl or an amine to be protected during a synthesis, and secondly allows the intact reactive function to be regenerated at the end of the synthesis. Examples of protecting groups and of protection and deprotection methods are given in "Protective Groups in Organic Synthesis", Greene et al., 3rd Edition (John Wiley & Sons, Inc., New York).

In the text hereinbelow, the term "leaving group" (T) means a group that can be readily cleaved from a molecule by breaking a heterolytic bond, with loss of an electron pair. This group may thus be readily replaced with another group during a nucleophilic substitution reaction or during an organometallic coupling reaction, for example. Such leaving groups are, for example, halogens or an activated hydroxyl group such as a mesyl, tosyl, triflate, acetyl, etc. Examples of leaving groups and references for preparing them are given in "Advances in Organic Chemistry", J. March, 3rd Edition, Wiley Interscience, p. 310-316.

In accordance with the invention, the compounds of formula (I) may be prepared according to the process that follows, which is illustrated in synthetic scheme No. 1.

The peptide coupling performed between the acid (II) and amines of formula (III) in the presence of a coupling agent such as N-{(1H-benzotriazol-1-yloxy)(dimethylamino)methylidene}-N-methylmethanaminium tetra-fluoroborate (TBTU) or N-[3-(dimethylamino)propyl-N'-ethylcarbodiimide hydrochloride (EDC.HCl) with or without N-hydroxysuccinimide (HONSu) and an organic base such as N,N-diisopropylethylamine (DIEA) and in a polar aprotic solvent such as acetonitrile or DMF, makes it possible to obtain the compounds of formula (I) in accordance with the invention (step i). The amines of formula (III) are synthesized according to methods known to those skilled in the art.

When R3=C(O)R5 with R5 representing a (C1-C4) alkoxy group, the compounds of formula (I) may also be saponified using a strong mineral base such as sodium hydroxide in a binary mixture such as water/methanol maintained at room temperature or heated to reflux to give, after acidification, the acids of formula (IV) (step ii).

Synthetic scheme 1:

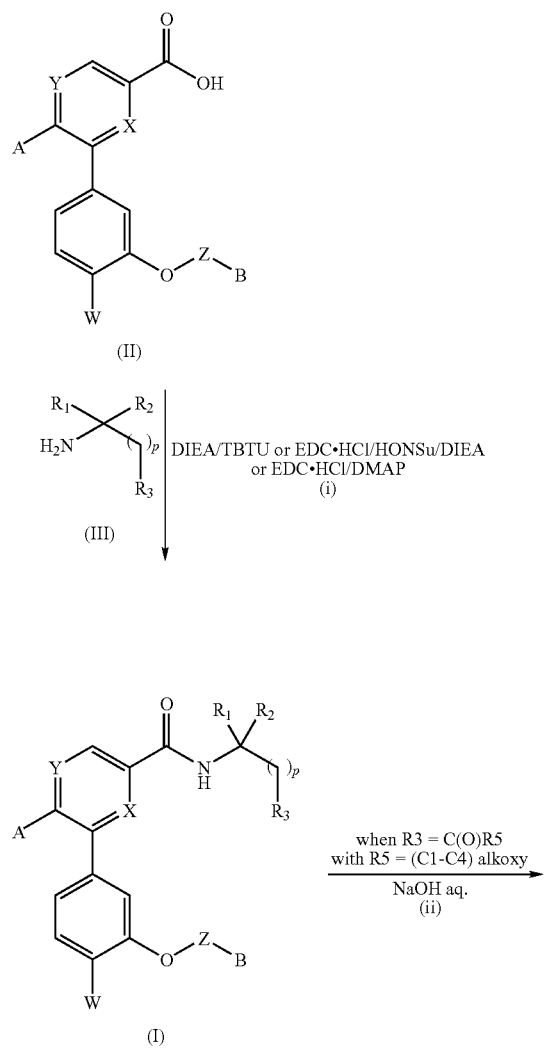

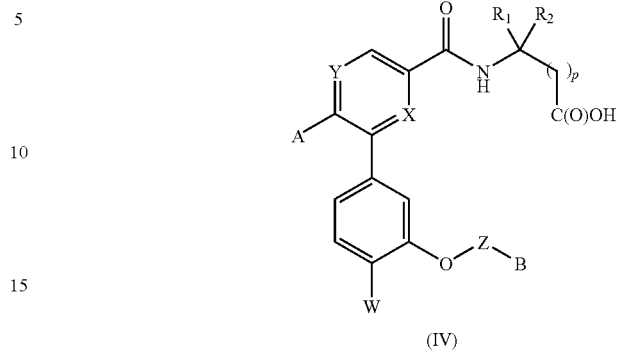

In another manner, compounds of formula (Ia), which correspond to compounds of formula (I) for which R3=C(O)R5, may be prepared according to the process that follows, which is illustrated in synthetic scheme No. 2:

The reaction between the acid (IV) and the alcohol or the amine R5H in the presence of thionyl chloride (SOCl$_2$) or of a peptide coupling agent such as TBTU or the EDC.HCl/HONSu system, an organic base such as DIEA and in a polar aprotic solvent such as acetonitrile or DMF makes it possible to obtain the compounds of formula (Ia) in accordance with the invention (step i).

More particularly, the compounds of formula (Ib), which correspond to compounds of formula (I) for which R3=—CH$_2$XR8, X being an oxygen atom and R8 being a hydrogen atom, may be prepared by reducing the acid (IV) with the aid of a reducing agent such as the borane/dimethyl sulfide complex and in an aprotic solvent such as THF (step ii).

Synthetic scheme 2:

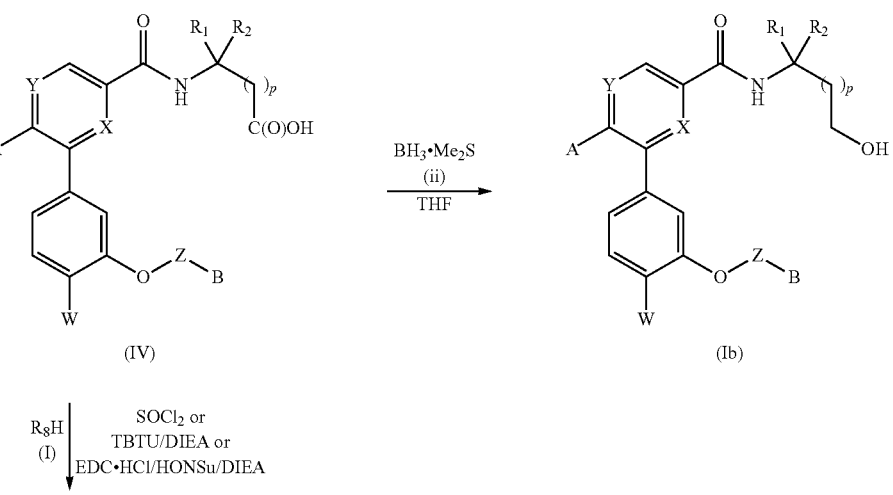

-continued

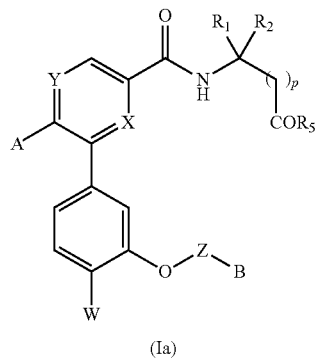

(Ia)

Compounds (II) and (IV) may be prepared according to the process that follows, illustrated in Scheme 3.

When, in the starting compound of formula (XIII), X represents a nitrogen atom, Y represents a carbon atom (i.e. a group of formula —CR4- as defined in relation with the compounds of formula (I) according to the invention), or alternatively X represents a carbon atom, Y represents a nitrogen atom, or alternatively X and Y represent a nitrogen atom, then a coupling reaction of Suzuki type catalyzed with a palladium(0) derivative such as tetrakis-(triphenylphosphine) palladium(0) [Pd(PPh$_3$)$_4$] or a palladium(II) derivative such as [1,1'-bis(cyclopentadienyldiphenylphosphino)ferrocene] palladium(II) dichloride [PdCl$_2$(dppf)] may be performed in a step (i) between the compound of formula (XIII) (in which Q=OH or Br and T=halogen atom, such as a bromine or iodine atom) and a boronic acid of formula (XI), in which PG represents a benzyl group optionally substituted with one or more alkoxy groups, in the presence of a weak mineral base such as potassium phosphate or K$_2$CO$_3$ and in a polar aprotic solvent such as N,N-dimethylformamide (DMF) or 1,4-dioxane at a temperature of about 95° C. This reaction makes it possible to regioselectively substitute the function T with the phenoxy nucleus (XI) to give compound (X).

The OH function of compound (X) is then converted into a leaving group such as trifluoromethanesulfonate (OTf), in step (ii), using trifluoromethane-sulfonic anhydride in the presence of a base such as triethylamine (TEA) and in a solvent such as dichloromethane (DCM) to give the compound of formula (IX).

The trifluoromethanesulfonate group thus obtained makes it possible in step (iii), by virtue of its reactivity, to introduce the nucleus A via an organo-palladium coupling reaction:
 either of the Suzuki type between compound (IX) and a boronic acid or ester of respective formulae A-B(OH)$_2$ or

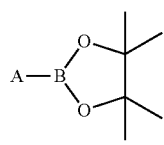

in the presence of a catalytic amount of a palladium derivative such as Pd(PPh$_3$)$_4$, in the presence of a weak mineral base such as potassium phosphate and of a polar aprotic solvent such as DMF, at a temperature of 90° C.;
 or of the Stille type between compound (IX) and an aryl-tributyl-stannane or heteroarylstannane derivative ASnBu$_3$ in the presence of a catalytic amount of copper iodide (CuI) and of a palladium(II) derivative such as PdCl$_2$(dppf) and of a polar aprotic solvent such as 1,4-dioxane at a temperature of 90° C.

Compound (VIII) is thus obtained.

Alternatively, an inversion of reactivity may be achieved by carrying out a sequence of two reactions: Borylation/Suzuki-Myaura (steps iv and v, respectively) starting with derivative (IX) and an aryl or heteroaryl halide A-T (T represents a halogen atom such as a bromine or iodine atom). The Suzuki-Myaura reaction is performed on intermediate (XII) in the presence of a catalytic amount of a palladium(0) derivative such as Pd(PPh$_3$)$_4$, a weak mineral base such as potassium carbonate, and in a binary mixture of solvents such as DME/water at a temperature of about 80° C. Furthermore, the dioxoborolanyl function of derivative (XII) is obtained from the trifluoromethanesulfonyl group of derivative (IX), by reaction with 4,4,4',4',5,5,5',5'-octamethyl-2,2'-bi-1,3,2-dioxaborolane in the presence of a catalytic amount of a palladium(II) derivative such as PdCl$_2$(dppf), a weak base such as potassium acetate, and in an apolar solvent such as toluene at a temperature of about 110° C.

Compound (VIII) is thus obtained.

The deprotection of the phenol function of the compound of formula (VIII) with boron tribromide at −78° C., trifluoroacetic acid (TFA) at room temperature or hydrogen chloride at 0° C. in DCM (step (vi)) gives the compound of formula (VII).

The introduction of the group Z-B in step (vii) may be performed:
 either via alkylation of compound (VII) with a chloro derivative Cl—Z—B in the presence of a weak mineral base such as cesium carbonate and in a polar aprotic solvent such as DMF at a temperature of between 80 and 100° C., such as 90° C.,
 or via a Mitsunobu reaction between compound (VII) and an alcohol of formula HO—Z—B in the presence of triphenylphosphine, diisopropyl azodicarboxylate (DIAD) and a catalytic amount of a weak organic base such as TEA at 0° C. in an aprotic solvent such as tetrahydrofuran (THF).

The compound of formula (VI) is then saponified in step (viii), using a strong mineral base such as potassium hydroxide in a water/methanol mixture maintained at room temperature or heated to reflux, to give, after acidification with a strong acid such as 1N hydrochloric acid (HCl), compound (II).

In the context of the present invention, the term "room temperature" means a temperature of between 20 and 25° C.

A peptide coupling reaction (step (ix)) between compound (II) and amines of formula (V) in the presence of a coupling agent such as carbonyld-iimidazole (CDI), N-[(1H-benzotriazol-1-yloxy)(dimethylamino)methylidene]-N-methylmethanaminium tetrafluoroborate (TBTU) or the EDC.HCl/HONSu system and an organic base such as DIEA and in a polar aprotic solvent such as DMF or N-methylpyrrolidinone (NMP) or acetonitrile at room temperature gives the compounds of formula (IV).

Scheme 3

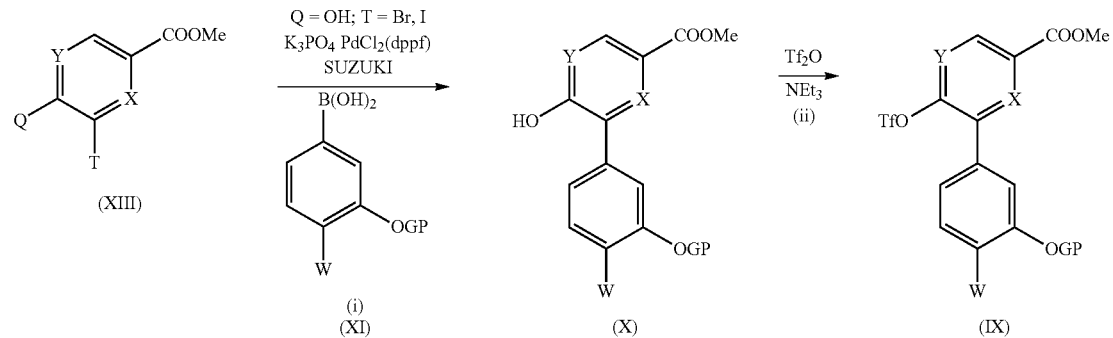

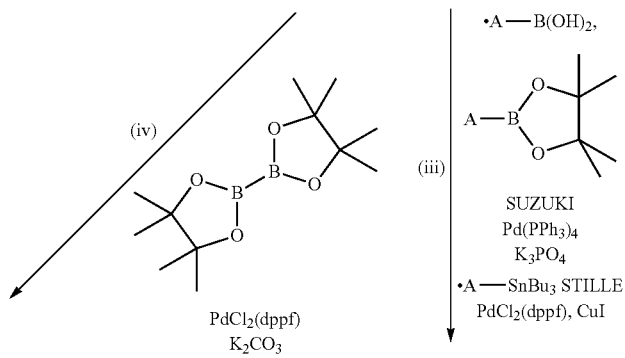

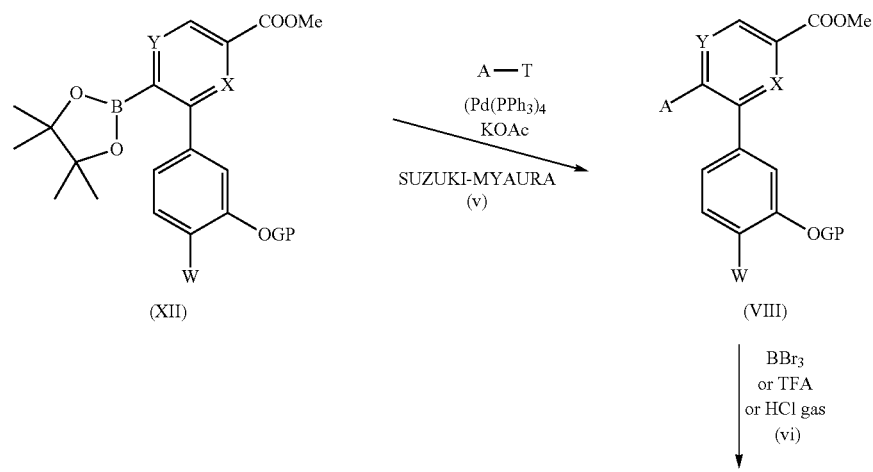

In Schemes 1, 2 and 3, the starting compounds and the reagents, when their modes of preparation are not described, are commercially available or described in the literature, or alternatively may be prepared according to methods that are described therein or that are known to those skilled in the art.

According to another of its aspects, a subject of the invention is also the compounds of formula (II). These compounds are useful as intermediates in the synthesis of the compounds of formula (I).

The examples that follow describe the preparation of certain compounds in accordance with the invention. These examples are not limiting, but serve merely to illustrate the present invention. The numbers of the compounds presented as examples refer to those given in the tables hereinbelow, which illustrates the chemical structures and physical properties of a number of compounds according to the invention.

The following abbreviations and empirical formulae are used:
EtOAc ethyl acetate
AcOH acetic acid
BSA N,O-bis(trimethylsilyl)acetamide
CDI carbonyldiimidazole
CuI copper iodide
DCM dichloromethane
DIBAL-H diisobutylaluminum hydride
DIAD diisopropyl azodicarboxylate
DIEA N,N-diisopropylethylamine
DMAP 4-dimethylaminopyridine
DME dimethoxyethane
DMF dimethylformamide
DMSO dimethyl sulfoxide
EDC.HCl N-[3-(dimethylamino)propyl-N'-ethylcarbodiimide hydrochloride
EtOH ethanol
h hour(s)
min minute(s)
HCl hydrochloric acid
$K_2CO_3$ potassium carbonate
KOAc potassium acetate
KOH sodium hydroxide
$K_3PO_4$ potassium phosphate or tripotassium tetraoxophosphate
$Na_2CO_3$ sodium carbonate
$NH_4Cl$ ammonium chloride
$NaHCO_3$ sodium hydrogen carbonate
$Na_2SO_4$ sodium sulfate
NMP N-methylpyrrolidinone
$PdCl_2(dppf)$ [1,1'-bis(cyclopentadienyldiphenylphosphino)ferrocene]-palladium(II) dichloride
$Pd(PPh_3)_4$ tetrakis(triphenylphosphine)palladium(0)
$Pd_2(dba)_3$ tris(dibenzylideneacetone)dipalladium(0)
TBTU N-[(1H-benzotriazol-1-yloxy)(dimethylamino)methylidene]-N-methylmethanaminium tetrafluoroborate
TEA triethylamine
TFA trifluoroacetic acid
THF tetrahydrofuran
R.T. room temperature The mass spectra are obtained under the following LC/MS coupling conditions:

Column: Kromasil 50×2.1 mm 6.5 μm
Eluents: A=$CH_3CN$/TFA (1000/0.5)
B=$H_2O$/$CH_3CN$/TFA (1000/30/0.5)

Gradients

| t(mm) | % A | % B | Flow rate (ml/mm) |
|---|---|---|---|
| 0 | 0 | 100 | 0.5 |
| 12 | 100 | 0 | 0.5 |
| 15 | 100 | 0 | 0.5 |

The retention time is noted by Tr.

The proton magnetic resonance spectra ($^1$H NMR), as described below, are recorded at 400 MHz in DMSO-$d_6$, using the peak of DMSO-$d_5$ as reference. The chemical shifts δ are expressed in parts per million (ppm). The signals observed are expressed as follows: s=singlet; d=doublet; t=triplet; m=multiplet or broad singlet; H=proton.

EXAMPLE 1

Methyl 1-{[(3,5-dichloro-2'-{4-chloro-3-[3-(dimethylamino)propoxy]-phenyl}-2,3'-bipyridin-6'-yl)carbonyl]amino}cyclohexane-carboxylate hydrochloride (Compound 1)

The synthesis of methyl 6-bromo-5-hydroxy-2-pyridinecarboxylate is performed according to a process already described in the literature (*J. Org. Chem.*, 1996, 4623-4633).

1.1
2-[(4-Methoxybenzyl)oxy]-1-chloro-4-iodobenzene

A suspension of 300 g (1179 mmol) of 2-chloro-5-iodophenol, 184 g (1179 mmol) of 4-methoxybenzyl chloride and 195.5 g (1415 mmol) of anhydrous $K_2CO_3$ in 1.2 L of anhydrous DMF is stirred for 5 hours at 70° C. and then cooled to room temperature. The reaction medium is then poured into 3 L of a 2/1 ether/water mixture. The organic phase is washed with 2×1 L of water, dried over $Na_2SO_4$ and concentrated under reduced pressure, and the residue obtained is solidified in pentane. 406 g of 2-[(4-methoxybenzyl)oxy]-1-chloro-4-iodobenzene are thus obtained in the form of a beige-colored powder.

Yield=92%
m.p. (° C.)=72.

1.2
[3-[(4-Methoxybenzyl)oxy]-4-chlorophenyl]boronic acid

To a solution of 145 g (387 mmol) of 2-[(4-methoxybenzyl)oxy]-1-chloro-4-iodobenzene in 1.2 L of anhydrous THF, placed under argon and stirred at −50° C., are added dropwise 220 mL (440 mmol) of a 2N solution of iPrMgCl in THF, while maintaining the temperature between −40 and −50° C. The reaction mixture is allowed to warm to −10° C. and stirring is continued for 1 hour. 94 mL (406 mmol) of triisopropyl borate are then added and the reaction mixture is then allowed to warm slowly to 0° C. After stirring for 2 hours, the mixture is treated with 500 mL of aqueous 5N HCl solution and then extracted with ether (2×600 mL). The organic phase is washed with 2×1 L of water, dried over $Na_2SO_4$ and concentrated under reduced pressure. The residue obtained is solidified in 300 mL of pentane, filtered off on a sinter funnel and washed with 200 mL of pentane. 96 g of [3-[(4-methoxybenzyl)oxy]-4-chlorophenyl]boronic acid are thus obtained in the form of a white solid.

Yield=84%
m.p. (° C.)=148 (decomposition).

1.3 Methyl 6-[3-[(4-methoxybenzyl)oxy]-4-chlorophenyl]-5-hydroxy-pyridine-2-carboxylate A solution of 80 g (345 mmol) of methyl 6-bromo-5-hydroxy-2-pyridine-carboxylate and 146 g (499 mmol) of [3-[(4-methoxybenzyl)oxy]-4-chloro-phenyl]boronic acid in 1600 mL of anhydrous dioxane is stirred for 15 minutes while sparging with argon, followed by addition of 143 g (1034 mmol) of anhydrous $K_2CO_3$ and 14 g (17.2 mmol) of $PdCl_2$ (dppf). The reaction medium is stirred for 10 hours at 95° C. under argon, cooled to room temperature and then poured at room temperature into 2 L of EtOAc and 350 mL of aqueous 1N HCl solution. The organic phase is washed with 300 mL of aqueous 1N HCl solution and 600 mL of water. After drying over $Na_2SO_4$ and concentrating under reduced pressure, the precipitate is taken up in 500 mL of a 7/3 pentane/DCM mixture, filtered and washed with 200 mL of pentane. 105 g of methyl 6-[3-[(4-methoxybenzyl)oxy]-4-chloro-phenyl]-5-hydroxypyridine-2-carboxylate are thus obtained in the form of a brown powder, which is used without further purification in the following step.

Yield=76%
m.p. (° C.)=202

1.4 Methyl 6-[3-[(4-methoxybenzyl)oxy]-4-chlorophenyl]-5-{[(trifluoro-methyl)sulfonyl]oxy}pyridine-2-carboxylate To a mixture of 115 g (287 mmol) of methyl 6-[3-[(4-methoxybenzyl)oxy]-4-chlorophenyl]-5-hydroxypyridine-2-carboxylate in 1200 mL of DCM are added 121.3 mL (863 mmol) of TEA. The mixture gradually dissolves and is cooled to −20° C. under argon. 54.5 mL (331 mmol) of trifluoromethane-sulfonic anhydride are added dropwise, while maintaining the temperature at −20° C. After 3 hours at −10° C., the reaction medium is taken up in 1 L of DCM and washed with 2×1 L of water, dried over $Na_2SO_4$ and then concentrated under reduced pressure. The residue obtained is purified by chromatography on a column of silica gel, eluting with a pentane/EtOAc gradient of from 0 to 30% EtOAc. After concentrating under reduced pressure, 138 g of methyl 6-[3-[(4-methoxybenzyl)oxy]-4-chlorophenyl]-5-{[(trifluoromethyl)sulfonyl]oxy}pyridine-2-carboxylate are obtained in the form of white crystals.

Yield=90%
m.p. (° C.)=89.

1.5 Methyl 6-[3-[(4-methoxybenzyl)oxy]-4-chlorophenyl]-5-(4,4,5,5-tetra-methyl-1,3,2-dioxaborolan-2-yl)pyridine-2-carboxylate A solution of 30 g (56 mmol) of methyl 6-[3-[(4-methoxybenzyl)oxy]-4-chlorophenyl-5-{[(trifluoromethyl)sulfonyl]oxy}pyridine-2-carboxylate and 28.6 g (113 mmol) of 4,4,4',4',5,5,5',5'-octamethyl-2,2'-bi-1,3,2-dioxa-borolane in 500 mL of anhydrous toluene is stirred for 15 minutes while sparging with argon, followed by addition of 16.6 g (169 mmol) of anhydrous KOAc and 2.3 g (2.82 mmol) of $PdCl_2$ (dppf), and the reaction mixture is heated for 26 hours at 110° C. The reaction mixture is then poured into 800 mL of a 1/1 EtOAc/brine mixture. The organic phase is dried over $Na_2SO_4$, filtered and then concentrated under reduced pressure. The residue obtained is purified by chromatography on a column of silica gel, eluting with a DCM/EtOAc gradient of from 0 to 30% EtOAc. After concentrating under reduced pressure, 22.4 g of methyl 6-[3-[(4-methoxy-benzyl)oxy]-4-chlorophenyl]-5-(4,4,5,5-tetramethyl-1,3,2-dioxaborolan-2-yl)pyridine-2-carboxylate are obtained in the form of a wax.
Yield=78%

1.6 Methyl 2'-[3-[(4-methoxybenzyl)oxy]-4-chlorophenyl]-3,5-dichloro-2,3'-bipyridine-6'-carboxylate To a suspension of 1 g (1.96 mmol) of methyl 6-[3-[(4-methoxybenzyl)oxy]-4-chlorophenyl]-5-(4,4,5,5-tetramethyl-1,3,2-dioxaborolan-2-yl)pyridine-2-carboxylate and 0.58 g (2.55 mmol) of 2-bromo-3,5-dichloropyridine in 10 mL of a 2/1 DME/water mixture, argon is sparged through for 10 minutes, followed by successive addition of 0.81 g (5.88 mmol) of $K_2CO_3$ and 0.159 g (0.14 mmol) of $Pd(PPh_3)_4$. The reaction mixture is heated for 4 hours at 80° C. and then cooled and diluted in 50 mL of EtOAc. The organic phase is washed with 2×20 mL of water, dried over $Na_2SO_4$ and then concentrated under reduced pressure. The residue is then purified on a column of silica gel, eluting with a cyclohexane/EtOAc gradient of from 0 to 40% EtOAc, to give 0.4 g of methyl 2'-[3-[(4-methoxybenzyl)oxy]-4-chlorophenyl]-3,5-dichloro-2,3'-bipyridine-6'-carboxylate in the form of an oil.
Yield=38%

1.7 Methyl 3,5-dichloro-2'-(4-chloro-3-hydroxyphenyl)-2,3'-bipyridine-6'-carboxylate To a solution of 0.4 g (0.75 mmol) of methyl 2'-[3-[(4-methoxybenzyl)oxy]-4-chlorophenyl]-3,5-dichloro-2,3'-pyridine-6'-carboxylate in 8 mL of anhydrous DCM cooled under argon to 0° C. is added 0.6 mL of TFA. After stirring at room temperature for 2 hours, the reaction medium is concentrated under reduced pressure. The residue obtained is taken up in 10 mL of EtOAc and 10 mL of saturated aqueous $NaHCO_3$ solution. After extraction, the aqueous phase is re-extracted with 10 mL of EtOAc. The organic phases are combined, washed with 10 mL of water, dried over $Na_2SO_4$ and concentrated under reduced pressure. The residue is purified by chromatography on a column of silica gel, eluting with a heptane/EtOAc gradient of from 0 to 30% EtOAc. After concentrating under reduced pressure, 0.27 g of methyl 3,5-dichloro-2'-(4-chloro-3-hydroxyphenyl)-2,3'-bipyridine-6'-carboxylate is obtained in the form of an oil.
Yield=89%

1.8 Methyl 3,5-dichloro-2'-{4-chloro-3-[3-(dimethylamino)propoxy]phenyl}-2,3'-bipyridine-6'-carboxylate To a solution of 2 g (4.88 mmol) of methyl 3,5-dichloro-2'-(4-chloro-3-hydroxyphenyl)-2,3'-bipyridine-6'-carboxylate in 20 mL of anhydrous DMF placed under argon are added 1.15 g (7.32 mmol) of 3-chloro-N,N-dimethylpropane-1-amine hydrochloride and 4.77 g (14.64 mmol) of cesium carbonate. The reaction medium is stirred for 18 hours at 90° C., cooled to room temperature and then concentrated under reduced pressure. The residue is taken up in 250 mL of EtOAc and washed with 250 mL of aqueous 5% $Na_2CO_3$ solution and then with 100 mL of water. After drying over $Na_2SO_4$ and concentrating under reduced pressure, the residue is purified by chromatography on a column of silica gel, eluting with a DCM/methanol gradient of from 0 to 15% methanol. After concentrating under reduced pressure, 1.82 g of methyl 3,5-dichloro-2'-{4-chloro-3-[3-(dimethylamino)propoxy]phenyl}-2,3'-bipyridine-6'-carboxylate is obtained in the form of a gum.
Yield=80%

1.9 3,5-Dichloro-2'-{4-chloro-3-[3-(dimethylamino)propoxy]phenyl}-2,3'-bipyridine-6'-carboxylic acid To a solution of 1.82 g (3.9 mmol) of 3,5-dichloro-2'-{4-chloro-3-[3-(dimethylamino)propoxy]phenyl}-2,3'-bipyridine-6'-carboxylate in 50 mL of EtOH and 10 ml of water is added 0.34 g (6.06 mmol) of KOH. The reaction medium is stirred for 18 hours at room temperature, and then concentrated under reduced pressure. The residue obtained is taken up in 6.1 mL of aqueous 1N HCl solution (6.1 mmol) and 100 ml of a 9/1 DCM/MeOH mixture. The organic phase is dried over $Na_2SO_4$ and then concentrated under reduced pressure, to give 1.8 g of 3,5-dichloro-2'-{4-chloro-3-[3-(dimethylamino)propoxy]phenyl}-2,3'-bipyridine-6'-carboxylic acid in the form of a gum.
Yield=95%

1.10 1-{[(3,5-Dichloro-2'-{4-chloro-3-[3-(dimethylamino)propoxy]phenyl}-2,3'-bipyridin-6'-yl)carbonyl]amino}cyclohexanecarboxylic acid hydro-chloride To a solution of 1.49 g (3.1 mmol) of 3,5-dichloro-2'-{4-chloro-3-[3-(dimethylamino)propoxy]phenyl}-2,3'-bipyridine-6'-carboxylic acid in 15 mL of anhydrous NMP are added under argon 1.62 mL (9.3 mmol) of DIEA and 2.83 g (8.82 mmol) of TBTU. In parallel, a mixture of 421 mg (2.94 mmol) of 1-aminocyclohexanecarboxylic acid and 1.51 mL (6.19 mmol) of BSA in 15 mL of anhydrous acetonitrile is brought to 90° C. with stirring and under argon. After 2 hours, the medium dissolves completely and the solution is cooled to room temperature and then added to the solution of 3,5-dichloro-2'-{4-chloro-3-[3-(dimethylamino)propoxy]phenyl}-2,3'-bipyridine-6'-carboxylic acid activated with TBTU. After stirring for 2 hours at room temperature, 10 mL of aqueous 0.5N HCl solution are added and stirring is continued for 18 hours. The reaction medium is then poured into a mixture of 100 mL of 9/1 DCM/MeOH and 10 mL of water. After extraction, the aqueous phase is again extracted with 10 mL of a 9/1 DCM/MeOH mixture. The organic phases are combined, dried over $Na_2SO_4$ and concentrated under reduced pressure. The residue is then purified by reverse-phase HPLC (RP18) using an aqueous $10^{-2}$N HCl/acetonitrile gradient of from 5% to 100% acetonitrile. After concentrating under reduced pressure and freeze-drying, 1 g of 1-{[(3,5-dichloro-2'-{4-chloro-3-[3-(dimethylamino)propoxy]phenyl}-2,3'-bipyridin-6'-yl)carbonyl]amino}cyclohexanecarboxylic acid hydrochloride is obtained in the form of a white powder.
Yield=50%
m.p. (° C.)=165

1.11 Methyl 1-{[(3,5-dichloro-2'-{4-chloro-3-[3-(dimethylamino)propoxy]-phenyl}-2,3'-bipyridin-6'-yl)carbonyl]amino}cyclohexanecarboxylate hydrochloride To a solution of 300 mg (0.47 mmol) of 1-{[(3,5-dichloro-2'-{4-chloro-3-[3-(dimethylamino)propoxy]phenyl}-2,3'-bipyridin-6'-yl)carbonyl]amino}cyclo-hexanecarboxylic acid hydrochloride in 10 mL of methanol and cooled to 0° C. is added 0.07 mL (0.93 mmol) of thionyl chloride. The reaction mixture is warmed to room temperature and stirred for 20 hours, and then concentrated under reduced pressure. The residue obtained is taken up in 20 mL of ether and solidified. After drying under reduced pressure, 268 mg of methyl 1-{[(3,5-dichloro-2'-{4-chloro-3-[3-(dimethylamino)propoxy]phenyl}-2,3'-bipyridin-6'-yl)carbonyl]amino}cyclohexanecarboxylate hydro-chloride are obtained in the form of a white powder.

Yield=87%
m.p. (° C.)=168
M=$C_{30}H_{33}Cl_3N_4O_4$=618; M+H=619; Tr=1.14 min.
$^1$H NMR (ppm, d6-DMSO, 400 MHz): 9.90 (s, 1H); 8.80 (s, 1H); 8.65 (s, 1H); 8.35 (s, 1H); 8.20 (d, 1H); 8.15 (d, 1H); 7.40 (d, 2H); 6.80 (d, 1H); 4.05 (m, 2H); 3.65 (s, 3H); 3.20 (m, 2H); 2.80 (s, 6H); 2.20 (m, 4H); 1.85 (t, 2H); 1.7-1.3 (m, 6H).

EXAMPLE 2

Methyl(3S)-3-({[6-{4-chloro-3-[3-(dimethylamino)propoxy]-phenyl}-5-(2-chlorophenyl)pyridin-2-yl]carbonyl}amino)-4,4-dimethylpentanoate hydrochloride (Compound 31)

2.1 Methyl 6-{4-chloro-3-[3-(dimethylamino)propoxy]phenyl}-5-(2-chlorophenyl)pyridine-2-carboxylate According to the debenzylation/O-alkylation/saponification sequence described in Examples 1.7, 1.8 and 1.9, respectively, starting with 665 mg (1.35 mmol) of methyl 6-[3-[(4-methoxybenzyl)oxy]-4-chlorophenyl]-5-(2-chlorophenyl)pyridine-2-carboxylate, 181 mg of 6-{4-chloro-3-[3-(dimethylamino)propoxy]phenyl}-5-(2-chlorophenyl)pyridine-2-carboxylic acid hydrochloride are obtained in the form of a gum.

Yield=28%

2.2 (3S)-3-({[6-{4-chloro-3-[3-(dimethylamino)propoxy]phenyl}-5-(2-chlorophenyl)pyridin-2-yl]carbonyl}amino)-4,4-dimethylpentanoic acid hydrochloride To a mixture of 674 mg (1.4 mmol) of 6-{4-chloro-3-[3-(dimethylamino)propoxy]phenyl}-5-(2-chlorophenyl)pyridine-2-carboxylic acid hydrochloride in 7 mL of anhydrous DMF are successively added, under argon and at room temperature, 240 mg (2.1 mmol) of N-hydroxysuccinimide and 401 mg (2.1 mmol) of EDC.HCl. After stirring for 18 hours, 1.31 mL (7.7 mmol) of DIEA and 304 mg (1.51 mmol) of tert-butyl(3S)-3-amino-4,4-dimethylpentanoate (*J. Org. Chem.*, 1999, 64, 6411-6417) are successively added to the reaction medium. Stirring is continued for 18 hours at room temperature and the reaction mixture is then concentrated under reduced pressure. The residue obtained is then treated for 18 hours at room temperature with 0.25 mL (3 mmol) of aqueous 12N HCl solution in 30 mL of formic acid and then concentrated under reduced pressure. After purification by reverse-phase HPLC (RP18), eluting with an aqueous $10^{-2}$N HCl/acetonitrile gradient of from 5% to 100% acetonitrile, and after freeze-drying, 500 mg of (3S)-3-({[6-{4-chloro-3-[3-(dimethylamino)propoxy]phenyl}-5-(2-chlorophenyl)pyridin-2-yl]carbonyl}-amino)-4,4-dimethylpentanoic acid hydrochloride are obtained in the form of a white powder.

Yield=59%
m.p. (° C.)=170

2.3 Methyl(3S)-3-({[6-{4-chloro-3-[3-(dimethylamino)propoxy]phenyl}-5-(2-chlorophenyl)pyridin-2-yl]carbonyl}amino)-4,4-dimethylpentanoate hydrochloride According to the procedure described in Example 1.11, esterification of 217 mg (0.356 mmol) of (3S)-3-({[6-{4-chloro-3-[3-(dimethylamino)propoxy]phenyl}-5-(2-chlorophenyl)pyridin-2-yl]carbonyl}amino)-4,4-dimethylpentanoic acid hydrochloride with 0.05 mL (0.71 mmol) of thionyl chloride in 4 mL of methanol gives, after solidification in 20 mL of ether and freeze-drying, 196 mg of methyl (3S)-3-({[6-{4-chloro-3-[3-(dimethylamino)propoxy]phenyl}-5-(2-chlorophenyl)pyridin-2-yl]carbonyl}amino)-4,4-dimethylpentanoate hydrochloride in the form of a white powder.

Yield=94%
m.p. (° C.)=126
$[\alpha]_D^{20}$=−17° (c=0.1, MeOH)
M=$C_{31}H_{37}Cl_2N_3O_4$=585; M+H=586; Tr=1.14 min
$^1$H NMR (ppm, d6-DMSO, 400 MHz): 10.15 (s, 1H); 8.45 (dd, 1H); 8.10 (dd, 1H); 8.05 (d, 1H); 7.55 (m, 1H); 7.45 (m, 3H); 7.40 (d, 1H); 7.20 (d, 1H); 6.95 (dd, 1H); 4.35 (td, 1H); 3.95 (m, 2H); 3.55 (d, 3H); 3.20 (m, 2H); 2.80 (d, 6H); 2.70 (m, 2H); 2.15 (m, 2H); 0.95 (d, 9H).

EXAMPLE 3

Methyl 1-{[(3-chloro-2'-{4-chloro-3-[3-(dimethylamino)-propoxy]phenyl}-5-methyl-2,3'-bipyridin-6'-yl)carbonyl]amino}cyclo-hexanecarboxylate hydrochloride (Compound 5)

3.1 Methyl 3-chloro-2'-{4-chloro-3-[(4-methoxybenzyl)oxy]phenyl}-5-methyl-2,3'-bipyridine-6'-carboxylate The Suzuki-Myaura coupling performed between 1 g (1.96 mmol) of methyl 6-[3-[(4-methoxybenzyl)oxy]-4-chlorophenyl]-5-(4,4,5,5-tetramethyl-1,3,2-dioxaborolan-2-yl)pyridine-2-carboxylate and 526 mg (2.55 mmol) of 2-bromo-3-chloro-5-methylpyridine according to Example 1.6 gives 637 mg of methyl 3-chloro-2'-{4-chloro-3-[(4-methoxybenzyl)oxy]phenyl}-5-methyl-2,3'-bipyridine-6'-carboxylate in the form of an oil.

Yield=64%

3.2 3-Chloro-2'-{4-chloro-3-[3-(dimethylamino)propoxy]phenyl}-5-methyl-2,3'-bipyridine-6'-carboxylic acid According to the debenzylation/O-alkylation/saponification sequence described in Examples 1.7, 1.8 and 1.9, respectively, starting with 338 mg (0.66 mmol) of methyl 3-chloro-2'-{4-chloro-3-[(4-methoxybenzyl)oxy]-phenyl}-5-methyl-2,3'-bipyridine-6'-carboxylate, 134 mg of 3-chloro-2'-{4-chloro-3-[3-(dimethylamino)propoxy]phenyl}-5-methyl-2, 3'-bipyridine-6'-carboxylic acid are obtained in the form of a brown gum.

Yield=45%

3.3 Methyl 1-aminocyclohexanecarboxylate hydrochloride

To a suspension of 2 g (14 mmol) of 1-aminocyclohexanecarboxylic acid in 20 mL of methanol is sparged hydrogen chloride for 2 minutes. 1.2 mL (16.8 mmol) of thionyl chloride are added to the solution obtained and the reaction medium is refluxed for 6 hours. After cooling, the mixture is concentrated under reduced pressure and the residue obtained is taken up in 5 mL of methanol. 50 mL of ether are added so as to precipitate 2.3 g of methyl 1-aminocyclohexanecarboxylate hydrochloride in the form of a white powder.

Yield=85% m.p. (° C.)=240

3.4 Methyl 1-{[(3-chloro-2'-{4-chloro-3-[3-(dimethylamino)propoxy]-phenyl}-5-methyl-2,3'-bipyridin-6'-yl)carbonyl]amino}cyclohexane-carboxylate hydrochloride To a suspension of 134 mg (0.29 mmol) of 3-chloro-2'-{4-chloro-3-[3-(dimethylamino)propoxy]phenyl}-5-methyl-2,3'-bipyridine-6'-carboxylic acid in 5 mL of anhydrous acetonitrile are successively added 0.18 mL (1.02 mmol) of DIEA and 56 mg (0.29 mmol) of methyl 1-aminocyclo-hexanecarboxylate hydrochloride. The mixture is cooled to 0° C. and 112 mg (0.35 mmol) of TBTU are added. After stirring for 18 hours between 0 and 10° C., the reaction medium is concentrated under reduced pressure and then taken up in 20 mL of a 1/1 EtOAc/ether mixture. After washing with 10 mL of water and 10 mL of saturated aqueous NaHCO$_3$ solution, the organic phase is dried over Na$_2$SO$_4$ and concentrated under reduced pressure. 0.2 mL (0.1 mmol) of a 2N solution of HCl in ether and then 20 mL of anhydrous ether are added to the residue, taken up in 5 mL of DCM, which allows precipitation of 139 mg of methyl 1-{[(3-chloro-2'-{4-chloro-3-[3-(dimethylamino)propoxy]phenyl}-5-methyl-2,3'-bipyridin-6'-yl)carbonyl]amino}cyclohexanecarboxylate hydrochloride in the form of a white powder.

Yield=80% m.p. (° C.)=152

M=C$_{31}$H$_{36}$Cl$_2$N$_4$O$_4$=598; M+H=599; Tr=1.11 min.

$^1$H NMR (ppm, d6-DMSO, 400 MHz): 10.25 (s, 1H); 8.60 (s, 1H); 8.52 (s, 1H); 8.10 (t, 2H); 7.85 (s, 1H); 7.40 (d, 1H); 7.35 (d, 1H); 6.90 (dd, 1H); 4.00 (m, 2H); 3.65 (s, 3H); 3.20 (m, 2H); 2.80 (d, 6H); 2.40 (s, 3H); 2.20 (m, 4H); 1.90 (t, 2H); 1.70-1.30 (m, 6H).

EXAMPLE 4

Methyl 1-({[6-{4-chloro-3-[3-(dimethylamino)propoxy]-phenyl}-5-(2-methylphenyl)pyridin-2-yl]carbonyl}amino)cyclohexanecarboxylate hydrochloride (Compound 4)

4.1 Methyl 6-[3-[(4-methoxybenzyl)]oxy-4-chlorophenyl]-5-(2-methyl-phenyl)pyridine-2-carboxylate A solution of 2.6 g (4.88 mmol) of methyl 6-[3-[(4-methoxybenzyl)oxy]-4-chlorophenyl]-5-{[(trifluoromethyl)sulfonyl]oxy}pyridine-2-carboxylate (Example 1.4) and 880 mg (6.48 mmol) of 2-methylphenylboronic acid in 20 mL of anhydrous DMF is stirred for 15 minutes while sparging with argon, followed by addition of 1.27 g (6 mmol) of anhydrous K$_3$PO$_4$ and 0.58 g (0.5 mmol) of Pd(PPh$_3$)$_4$, and the reaction mixture is stirred for 18 hours at 90° C. under argon. The reaction medium is then poured at room temperature into 120 ml of a 1/1/2 ether/EtOAc/water mixture. After extracting, the aqueous phase is re-extracted with 10 mL of EtOAc, the organic phases are combined and washed with 4×30 mL of water, dried over Na$_2$SO$_4$ and then concentrated under reduced pressure. The residue obtained is purified by chromatography on a column of silica gel, eluting with a heptane/EtOAc gradient of from 0 to 20% EtOAc. After concentrating under reduced pressure, 1.8 g of methyl 6-[3-[(4-methoxybenzyl)]oxy-4-chlorophenyl]-5-(2-methylphenyl)pyridine-2-carboxylate are obtained in the form of an oil.

Yield=81%

4.2 6-{4-Chloro-3-[3-(dimethylamino)propoxy]phenyl}-5-(2-methylphenyl)pyridine-2-carboxylic acid According to the debenzylation/O-alkylation/saponification sequence described in Examples 1.7, 1.8 and 1.9, respectively, starting with 5.3 g (11 mmol) of methyl 6-[3-[(4-methoxybenzyl)]oxy-4-chlorophenyl]-5-(2-methylphenyl)pyridine-2-carboxylate and 1.4 g (8.9 mmol) of 3-chloro-N,N-dimethylpropane-1-amine hydrochloride, 3.9 g of 6-{4-chloro-3-[3-(dimethylamino)propoxy]phenyl}-5-(2-methylphenyl)pyridine-2-carboxylic acid are obtained in the form of a gum.

Yield=81% m.p. (° C.)=146-150

4.3 Methyl 1-({[6-{4-chloro-3-[3-(dimethylamino)propoxy]phenyl}-5-(2-methylphenyl)pyridin-2-yl]carbonyl}amino)cyclohexanecarboxylate hydrochloride According to the procedure described in Example 3.5, the peptide coupling performed between 300 mg (0.71 mmol) of 6-{4-chloro-3-[3-(dimethylamino)propoxy]phenyl}-5-(2-methylphenyl)pyridine-2-carboxylic acid and 137 mg (0.71 mmol) of methyl 1-aminocyclohexanecarboxylate hydrochloride gives, after solidification, 190 mg of methyl 1-({[6-{4-chloro-3-[3-(dimethylamino)propoxy]phenyl}-5-(2-methylphenyl)pyridin-2-yl]carbonyl}-amino)cyclohexanecarboxylate hydrochloride in the form of a white powder.

Yield=48% m.p. (° C.)=115

M=C$_{32}$H$_{38}$ClN$_3$O$_4$=563; M+H=564; Tr=1.18 min.

$^1$H NMR (ppm, d6-DMSO, 400 MHz): 10.2 (s, 1H); 8.55 (s, 1H); 8.10 (d, 1H); 7.95 (d, 1H); 7.40-7.20 (m, 6H); 7.05 (dd, 1H); 3.85 (m, 2H); 3.65 (s, 3H); 3.20 (m, 2H); 2.80 (d, 6H); 2.20 (d, 2H); 2.10 (m, 2H); 1.90 (s, 3H); 1.85 (t, 2H); 1.70-1.30 (m, 6H).

EXAMPLE 5

Methyl cis-1-({[6-{4-chloro-3-[3-(dimethylamino)propoxy]-phenyl}-5-(2-methylphenyl)pyridin-2-yl]carbonyl}amino)-4-hydroxy-cyclohexanecarboxylate hydrochloride (Compound 42)

5.1 Methyl cis-1-amino-4-hydroxycyclohexanecarboxylate hydrochloride

According to the procedure described in Example 3.4, the esterification of 1.41 g (7.21 mmol) of cis-1-amino-4-hydroxycyclohexanecarboxylic acid (*J. Chem. Soc., Perkin Trans.* 1 (1999) pp. 3375-3379) with 0.62 mL (8.65 mmol) of thionyl chloride in 30 mL of methanol gives 1.5 g of methyl cis-1-amino-4-hydroxycyclohexanecarboxylate hydrochloride in the form of a white powder.

Yield=100% m.p. (° C.)=160

5.2 Methyl cis-1-({[6-{4-chloro-3-[3-(dimethylamino)propoxy]phenyl}-5-(2-methylphenyl)pyridin-2-yl]carbonyl}amino)-4-hydroxycyclohexanecarboxylate hydrochloride To a suspension of 467 mg (1.1 mmol) of 6-{4-chloro-3-[3-(dimethylamino)propoxy]phenyl}-5-(2-methylphenyl)pyridine-2-carboxylic acid (Example 4.2) in 11 mL of anhydrous DMF are successively added, under argon and at room temperature, 139 mg (1.21 mmol) of N-hydroxysuccinimide and 232 mg (1.21 mmol) of EDC.HCl. The reaction mixture is stirred for 24 hours at room temperature, followed by addition to the clear yellow solution of 253 mg (1.21 mmol) of methyl cis-1-amino-4-hydroxycyclohexanecarboxylate hydrochloride and 1 mL (5.94 mmol) of DIEA. After stirring for a further 16 hours at room temperature, the reaction medium is diluted in 30 mL of EtOAc and the organic phase is washed with 3×20 mL of water. After drying over $Na_2SO_4$ and concentrating under reduced pressure, the residue obtained is taken up in a mixture of 5 mL of methanol and 1.5 mL of aqueous 1N HCl solution (1.5 mmol) and then purified by reverse-phase HPLC (RP18), eluting with an aqueous $10^{-2}$N HCl/acetonitrile gradient of from 5% to 100% acetonitrile over 90 minutes. After concentrating under reduced pressure and freeze-drying, 252 mg of methyl cis-1-({[6-{4-chloro-3-[3-(dimethylamino)propoxy]phenyl}-5-(2-methylphenyl)pyridin-2-yl]carbonyl}amino)-4-hydroxycyclohexanecarboxylate hydrochloride are obtained in the form of a white powder.

Yield=37%
m.p. (° C.)=244° C.
M=$C_{32}H_{38}ClN_3O_5$=579; M+H=580; Tr=7.2 min (gradient of 20 min.).
$^1$H NMR (ppm, d6-DMSO, 400 MHz): 9.80 (s, 1H); 8.60 (s, 1H); 8.05 (d, 1H); 7.95 (d, 1H); 7.35 (d, 1H); 7.30-7.10 (m, 5H); 6.95 (dd, 1H); 4.75 (m, 1H); 3.95 (m, 2H); 3.65 (s, 3H); 3.55 (m, 1H); 3.20 (m, 2H); 2.85 (s, 6H); 2.30 (m, 2H); 2.15 (m, 2H); 1.90 (s, 3H); 1.80 (m, 4H); 1.40 (m, 2H).

EXAMPLE 6

6-{4-Chloro-3-[3-(dimethylamino)propoxy]phenyl}-N-[(1S)-2,2-dimethyl-1-{2-[(methylsulfonyl)amino]-2-oxoethyl}propyl]-5-(2-methylphenyl)pyridine-2-carboxamide hydrochloride (Compound 34)

6.1 (3S)-3-({[6-{4-chloro-3-[3-(dimethylamino)propoxy]phenyl}-5-(2,4-dimethylphenyl)pyridin-2-yl]carbonyl}amino)-4,4-dimethylpentanoic acid hydrochloride According to the process described in Example 2.2, the peptide coupling performed between 425 mg (1 mmol) of 6-{4-chloro-3-[3-(dimethylamino)propoxy]phenyl}-5-(2-methylphenyl)pyridine-2-carboxylic acid (Example 4.2) and 206 mg (2.05 mmol) of tert-butyl(3S)-3-amino-4,4-dimethylpentanoate (*J. Org. Chem.*, 1999, 64, 6411-6417) gives 390 mg of (3S)-3-({[6-{4-chloro-3-[3-(dimethylamino)propoxy]phenyl}-5-(2-methylphenyl)pyridin-2-yl]carbonyl}amino)-4,4-dimethylpentanoic acid hydrochloride in the form of a white powder.

Yield=66%
m.p. (° C.)=130
$[\alpha]_D^{20}$=−5°; (c=0.1; MeOH)

6.2 6-{4-Chloro-3-[3-(dimethylamino)propoxy]phenyl}-N-[(1S)-2,2-dimethyl-1-{2[(methylsulfonyl)amino]-2-oxoethyl)propyl]-5-(2-methylphenyl)pyridine-2-carboxamide hydrochloride To a solution of 250 mg (0.42 mmol) of (3S)-3-({[6-{4-chloro-3-[3-(dimethylamino)propoxy]phenyl}-5-(2-methylphenyl)pyridin-2-yl]-carbonyl}amino)-4,4-dimethylpentanoic acid hydrochloride and 49 mg (0.51 mmol) of methanesulfonamide in 2 mL of DCM are successively added 52 mg (0.42 mmol) of DMAP and 89 mg (0.47 mmol) of EDC.HCl. The reaction medium is stirred for 16 hours at room temperature. A further 0.42 mmol of EDC.HCl and 0.42 mmol of methanesulfonamide are added and the reaction mixture is stirred for a further 3 days and then concentrated under reduced pressure. The residue is taken up in 100 mL of EtOAc and the organic phase is washed with 30 mL of water and then with 30 mL of aqueous 4M $NaHCO_3$ solution. After drying over $Na_2SO_4$ and concentrating under reduced pressure, the residue is purified by chromatography on a column of silica gel, eluting with a DCM/methanol gradient of from 0 to 10% methanol. After concentrating under reduced pressure, the residue is taken up in 2 mL of methanol and 0.5 mL of aqueous 1N HCl solution and then purified by reverse-phase HPLC (RP18), eluting with a $10^{-2}$N HCl/acetonitrile gradient of from 5% to 100% acetonitrile over 90 minutes. After concentrating under reduced pressure and freeze-drying, 130 mg of 6-{4-chloro-3-[3-(dimethylamino)propoxy]phenyl}-N-[(1S)-2,2-dimethyl-1-{2[(methylsulfonyl)amino]-2-oxoethyl}propyl]-5-(2-methylphenyl)pyridine-2-carboxamide hydrochloride are obtained in the form of a white powder.

Yield=46%
m.p. (° C.)=138° C.
$[\alpha]_D^{20}$=−45°; (c=0.5; MeOH)
M=$C_{32}H_{41}ClN_4O_5S$=628; M+H=629; Tr=1.06 min.
$^1$H NMR (ppm, d6-DMSO, 400 MHz): 11.80 (d, 1H); 10.30 (s, 1H); 8:40 (t, 1H); 8.05 (d, 1H); 7.95 (d, 1H); 7.30 (m, 5H); 7.15 (d, 1H); 7.05 (dd, 1H); 4.35 (t, 1H); 3.80 (m, 2H); 3.15 (m, 2H); 3.05 (s, 3H); 2.80 (s, 6H); 2.65 (m, 2H); 2.10 (m, 2H); 1.90 (s, 3H); 1.00 (d, 9H).

EXAMPLE 7

6-{4-Chloro-3-[3-(dimethylamino)propoxy]phenyl}-N-[(1S)-1-(2-hydroxyethyl)-2,2-dimethylpropyl]-5-(2-methylphenyl)pyridine-2-carboxamide hydrochloride (Compound 37)

To a solution of 250 mg (0.42 mmol) of (3S)-3-({[6-{4-chloro-3-[3-(dimethylamino)propoxy]phenyl}-5-(2-methylphenyl)pyridin-2-yl]carbonyl}-amino)-4,4-dimethylpentanoic acid hydrochloride (Example 6.1) in 2 mL of THF are added dropwise, under argon, 1.06 mL (2.12 mmol) of a 2N borane/dimethyl sulfide complex solution in THF. The reaction medium is stirred for 16 hours at room temperature and then diluted in 10 mL of anhydrous methanol. The solution obtained is concentrated under reduced pressure and the residue is taken up in 20 mL of methanol and then concentrated again under reduced pressure. The residue obtained is then dissolved in 20 mL of a 1/1 THF/aqueous 1N HCl solution mixture and the solution is refluxed for 4 hours. After cooling and concentrating under reduced pressure, the residue is purified by reverse-phase HPLC (RP18), eluting with a $10^{-2}$N HCl/acetonitrile gradient of from 0 to 100% acetonitrile over 120 minutes. After concentrating under reduced pressure and freeze-drying, 50 mg of 6-{4-chloro-3-[3-(dimethylamino)

propoxy]phenyl}-N-[(1S)-1-(2-hydroxyethyl)-2,2-dimethylpropyl]-5-(2-methylphenyl)pyridine-2-carboxamide hydrochloride are obtained in the form of a white powder.

Yield=20% m.p. (° C.)=93

$[\alpha]_D^{20}=-20°$ (c=0.4, MeOH)

$M=C_{31}H_{40}ClN_3O_3=537$; M+H=538; Tr=1.06 min.

$^1$H NMR (ppm, d6-DMSO, 400 MHz): 10.10 (s, 1H); 8.15 (d, 1H); 8.10 (dd, 1H); 7.95 (d, 1H); 7.30 (m, 5H); 7.10 (m, 1H); 7.05 (dd, 1H); 3.95 (t, 1H); 3.80 (m, 2H); 3.45 (m, 2H); 3.15 (m, 2H); 2.80 (d, 6H); 2.10 (m, 2H); 1.90 (d, 3H); 1.85 (m, 1H); 1.65 (m, 1H); 0.95 (d, 9H).

The tables that follow illustrate the chemical structures and physical properties of a number of examples of compounds according to the invention.

The compounds described in the tables were all obtained in hydrochloride form.

Table 1 illustrates compounds of formula (Ic) corresponding to compounds of formula (I) for which W represents a chlorine atom, Z represents —$(CH_2)_3$— and B represents —$N(CH_3)_2$.

Table 2 illustrates compounds of formula (Id) corresponding to compounds of formula (I) for which W represents a chlorine atom, Z represents —$(CH_2)_3$— and B represents —$N(CH_3)_2$, p is equal to 0 and R3 represents C(O)OMe.

In these tables:

Me, Et and i-Pr represent, respectively, methyl, ethyl and isopropyl groups,

C(O)Oalkyl represents an ester function, for example C(O)OMe represents a methyl ester function, C(O)OiPr represents an isopropyl ester function, etc., $C(O)NH_2$ represents an amide function, etc., the m.p. column indicates the melting point, in ° C., of the compound.

TABLE OF COMPOUNDS

TABLE 1

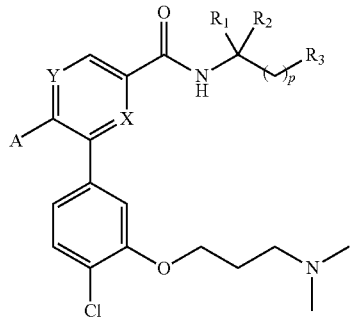

(Ic)

| No. | A | p | R₂ | R₁ | X | Y | R₃ | Melting point (° C.) |
|---|---|---|---|---|---|---|---|---|
| 1 Ex1 | 3,5-dichloro-2-methylpyridin-yl | 0 | cyclohexyl | * | N | CH | C(O)OMe | 168 |
| 2 | 3-methyl-4-methyl-phenol (4-hydroxy-2,3-dimethylphenyl) | 0 | cyclohexyl | * | N | CH | C(O)OMe | 270 |
| 3 | 2,3-dimethyl-4-hydroxyphenyl | 0 | cyclohexyl | * | N | CH | C(O)OMe | 166 |
| 4 Ex 4 | 2-methylphenyl | 0 | cyclohexyl | * | N | CH | C(O)OMe | 115 |

TABLE 1-continued (Ic)

| No. | A | p | R₂ | R₁ | X | Y | R₃ | Melting point (° C.) |
|---|---|---|---|---|---|---|---|---|
| 5 Ex 3 | 3-chloro-2,5-dimethylpyridin-4-yl | 0 | cyclohexyl | | N | CH | C(O)OMe | 152 |
| 6 | 3-methyl-4-(2-methoxyethoxy)... (Me, with 2-methoxyethoxy substituent) | 0 | cyclohexyl | | N | CH | C(O)OMe | 200 |
| 7 | 3-methyl-4-cyclopropyl-phenyl (Me) | 0 | cyclohexyl | | N | CH | C(O)OMe | 114 |
| 8 | 3-methyl-4-isopropoxy-phenyl (Me) | 0 | cyclohexyl | | N | CH | C(O)OMe | 194 |
| 9 | 4-chloro-3-methyl...propoxy-phenyl (Cl) | 0 | cyclohexyl | | N | CH | C(O)OMe | 117 |

TABLE 1-continued
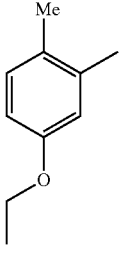
(Ic)
| No. | A | p | R₂ R₁ | X | Y | R₃ | Melting point (° C.) |
|---|---|---|---|---|---|---|---|
| 10 | 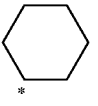 | 0 | 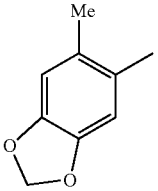 | N | CH | C(O)OMe | 116 |
| 11 |  | 0 |  | N | CH | C(O)OMe | 138 |
| 12 |  | 0 | 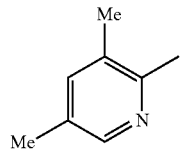 | N | CH | C(O)OMe | 160 |
| 13 |  | 0 | 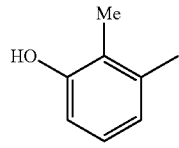 | N | CH | C(O)OMe | 176 |
| 14 |  | 0 | 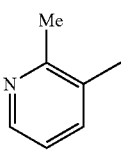 | N | CH | C(O)OMe | >250 |
| 15 |  | 0 |  | N | CH | C(O)OMe | 172 |

TABLE 1-continued (Ic)

| No. | A | p | R₂ R₁ | X | Y | R₃ | Melting point (° C.) |
|---|---|---|---|---|---|---|---|
| 16 | 4-(difluoromethoxy)-2-methylphenyl (Me top, OCHF₂ bottom) | 0 | cyclohexyl | N | CH | C(O)OMe | 119 |
| 17 | 2-(difluoromethyl)-4-methylphenyl (CHF₂ top, Me bottom) | 0 | cyclohexyl | N | CH | C(O)OMe | 124 |
| 18 | 1,3-dimethyl-5-methylpyrazolyl (Me, N-Me, Me) | 0 | cyclohexyl | N | CH | C(O)OMe | 158 |
| 19 | 1-methyl-3,5-diethylpyrazolyl (Et, N-Me, Et) | 0 | cyclohexyl | N | CH | C(O)OMe | 128 |
| 20 | 2,4-dimethylphenyl | 0 | cyclohexyl | N | N | C(O)OMe | 118 |

TABLE 1-continued
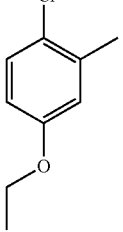
(Ic)
| No. | A | p | R₂ | R₁ | X | Y | R₃ | Melting point (° C.) |
|---|---|---|---|---|---|---|---|---|
| 21 |  | 0 | 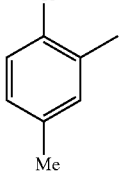 | | N | N | C(O)OMe | 124 |
| 22 | 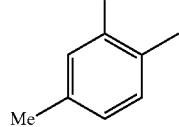 | 1 | CH(Me)₂ enantiomer (S) | H | N | CH | C(O)OMe | 166 |
| 23 | 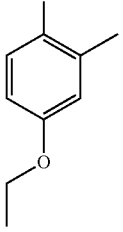 | 1 | C(Me)₃ enantiomer (S) | H | N | CH | C(O)OMe | 129 |
| 24 | 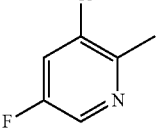 | 1 | C(Me)₃ enantiomer (S) | H | N | N | C(O)OMe | 112 |
| 25 | 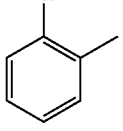 | 1 | C(Me)₃ enantiomer (S) | H | N | CH | C(O)OMe | 130 |
| 26 |  | 0 | | | N | CH | C(O)OMe | 135 |

TABLE 1-continued
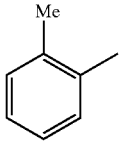
(Ic)
| No. | A | p | R$_2$ | R$_1$ | X | Y | R$_3$ | Melting point (° C.) |
|---|---|---|---|---|---|---|---|---|
| 27 | Me 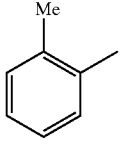 | 1 | C(Me)$_3$ enantiomer (S) | H | N | CH | C(O)O(CH$_2$)$_2$OCH$_3$ | 85 |
| 28 | Me 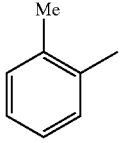 | 1 | C(Me)$_3$ enantiomer (S) | H | N | CH | C(O)OMe | 93 |
| 29 | Me 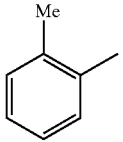 | 1 | C(Me)$_3$ enantiomer (S) | H | N | CH | C(O)OEt | 90 |
| 30 | Me 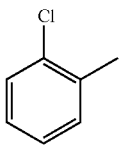 | 1 | C(Me)$_3$ enantiomer (S) | H | N | CH | C(O)OiPr | 190 |
| 31 Ex 2 | Cl 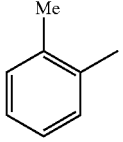 | 1 | C(Me)$_3$ enantiomer (S) | H | N | CH | C(O)OMe | 126 |
| 32 | Me 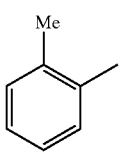 | 1 | C(Me)$_3$ enantiomer (S) | H | N | CH | C(O)NH$_2$ | 152 |
| 33 | Me | 1 | C(Me)$_3$ enantiomer (S) | H | N | CH | C(O)NHMe | 152 |

TABLE 1-continued
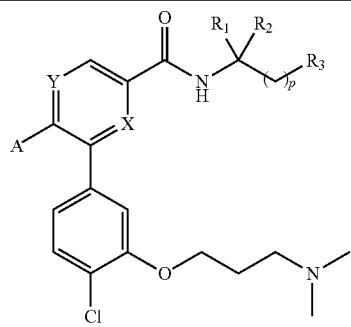
(Ic)
| No. | A | p | R₂ | R₁ | X | Y | R₃ | Melting point (° C.) |
|---|---|---|---|---|---|---|---|---|
| 34 Ex 6 | Me (o-tolyl) | 1 | C(Me)₃ enantiomer (S) | H | N | CH | C(O)NHSO₂Me | 138 |
| 35 | Me (o-tolyl) | 1 | C(Me)₃ enantiomer (S) | H | N | CH | C(O)NHCH₂CF₃ | 142 |
| 36 | Me (o-tolyl) | 1 | C(Me)₃ enantiomer (S) | H | N | CH | C(O)NH-cyclopropyl | 151 |
| 37 Ex 7 | Me (o-tolyl) | 1 | C(Me)₃ enantiomer (S) | H | N | CH | CH₂OH | 93 |
| 38 | Me (o-tolyl) | 1 | C(Me)₃ enantiomer (S) | H | N | CH | CH₂OMe | 108 |
| 39 | Me (o-tolyl) | 1 | C(Me)₃ enantiomer (S) | H | N | CH | CN | 140 |

TABLE 2

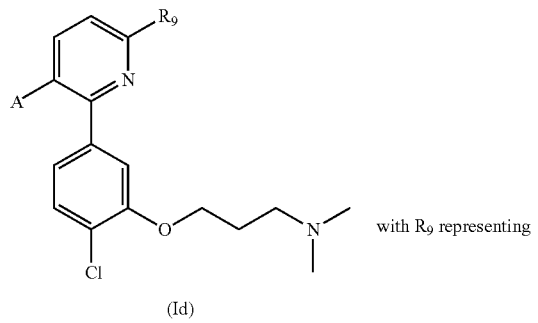 with R9 representing

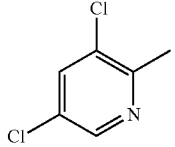

| No. | A | R9 | Melting point (° C.) |
|---|---|---|---|
| 40 | 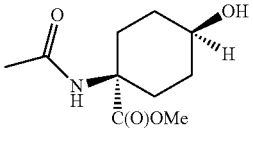 | 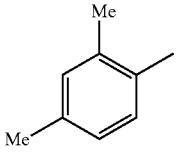 | 202 |
| 41 | 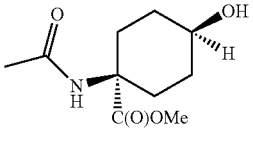 | 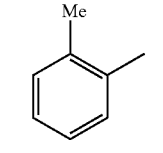 | 253 |
| 42 Ex 5 | 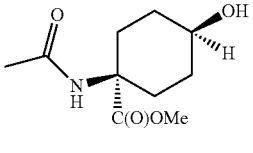 | 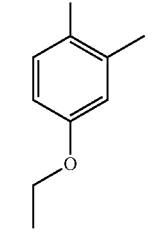 | 244 |
| 43 | 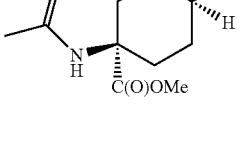 | 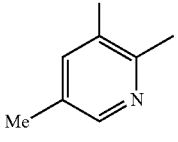 | 160 |
| 44 | 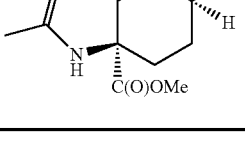 | | 178 |

The compounds according to the invention underwent pharmacological trials to determine the properties of the compounds of the invention, in particular with an in vitro test of intracellular calcium mobilization (FlipR test) using urotensin II antagonists (the compounds of the present invention) of human GPR14 receptor.

This test is described below:

1. FlipR Protocol (Fluorometric Imaging Plate Reader)

1.1 Objective

The objective is to measure the activation of the GPR14 receptor with human urotensin II.

1.2. Test Principle

GPR14 is a 7-domain transmembrane receptor coupled to Gq. Its activation with a specific ligand causes an increase in $Ca^{2+}$ in the cell via the PLC (phospholipase C), IP3 (inositol-1,4,5-triphosphate) DAG (diacylglycerol) route.

The increase in $Ca^{2+}$ in the cell is measured using a Fluo4AM permeating probe (monoexcitation, monoemission probe) which binds to the free $Ca^{2+}$ and emits at 520 nm. The free probe is nonfluorescent in the absence of $Ca^{2+}$.

1.3. Protocol
Experiment Plan
1) Seeding of the cells on D-1 (day-1) or D-2
2) Incorporation/charge (D0) of the probe (1 h)
3) Addition of the products to the FlipR and measurement
4) Addition of the ligand to the FlipR and measurement in the presence of the products
5) Processing and exportation of the data CHOGPR14 Cells The cells are cultured in whole medium in a T225 flask. For the experiments, the cells are subcultured in 200 µl of culture medium in transparent-bottomed black 96-well plates at a rate of 60 000 cells/well for a use on D+1 or 40 000 cells/well for a use on D+2.

Incorporation of the Fluo-4M

Fluo-4AM is prepared at 20 mM and then divided into aliquots (50 µl) and stored at −20° C. sheltered from light. A solution of pluronic acid at 200 mg/ml in DMSO is also prepared (it keeps for one week at room temperature sheltered from light).

The cells are charged with the mixture of Fluo-4AM+pluronic acid (aliquots of 50 µl+50 µl of pluronic acid) diluted to 1/100 in the measuring buffer.

After washing the wells with 150 µl of measuring buffer (cf. appendix), the cells are then charged in the following manner:

distribution of 100 µl of measuring buffer into each well
addition of 10 µl of the Fluo-4AM+pluronic acid mixture diluted to 1/100.

The cells are incubated for 1 hour at 37° C. sheltered from light, in an incubator in the presence of 5% $CO_2$.

The cells are then washed 3 times with 150 µl of measuring buffer to remove the excess probe. A volume of 150 µl of buffer is added to each well at the end of washing.

After incubating the plates for 20 minutes at room temperature sheltered from light, they are placed in the FlipR for the fluorescence measurement.

The basic level of incorporation of the Fluo-4 is checked for each plate (sd<10%) before the first injection.

After stabilizing the base signal, the GPR14 inhibitor compounds are injected via the FlipR in a volume of 50 µl using a dilution plate prepared with Biomek 2000 as measuring buffer. Urotensin II (3 nM final, concentration equal to the $EC_{50}$) is added in a volume of 50 µl via the FlipR to the cells using a stock plate at 15 nM diluted in the measuring buffer.

The data are recorded continuously throughout the experiment.

1.4. Data Analysis

For each plate, the base fluorescence before injection of the compounds is normalized via the "spatial uniformity correction" function of the FlipR. The fluorescence values measured just before injection of urotensin II (min) and those of the fluorescence measured at the peak of the urotensin II effect (max) are exported in Excel. In each plate, a series of wells is treated with urotensin alone in the absence of inhibitor compound. The min and max fluorescence values for these wells are averaged and make it possible to define the 100% effect of the urotensin II.

The inhibition percentages calculated for each inhibitor concentration are calculated in the following manner:

for each well Uro II (urotensin II)+inhibitor, calculation of the product delta value=max−min for the wells of Uro II alone, calculation of the Uro II delta value (average max−average min)

The percentage of inhibition for each concentration of product is calculated as described below:

Inhibition (%)=100×(delta Uro II−delta product)/delta Uro II 1.5. Appendix

Composition of the measuring buffer (in demineralized water, prepared extemporaneously)

|  | qs 500 mL | qs 1 L | qs 2 L |
|---|---|---|---|
| HBSS | 50 mL | 100 mL | 200 mL |
| $MgSO_4$ 19.72 g/L | 5 mL | 10 mL | 20 mL |
| Hepes | 2.38 g | 4.76 g | 9 52 g |
| $Na_2CO_3$ 35 g/L | 5 mL | 10 mL | 20 mL |
| $CaCl_2$ 14.7 g/L | 5 mL | 10 mL | 20 mL |
| BSA 10% | 50 mL | 100 mL | 200 mL |

HBSS = Hanks' Balanced Salt Solution
BSA = Bovine Serum Albumin

The various saline solutions may be stored for 2 months at 4° C.

Adjust the $H_2O$ volume and add probenecid dissolved in 1N sodium hydroxide

| +probenecid | 0.355 g in 5 mL of 1N NaOH | 0.71 g in 10 mL of 1N NaOH | 1.42 g in 20 mL of 1N NaOH |
|---|---|---|---|

Check the pH 7.4.
1.6. Materials
Human urotensin II (Bachem H-4768)
Fluo-4AM (Molecular Probes F14202 5×1 mg)
Probenecid (Sigma P8761 100 g)
Pluronic acid (Molecular Probes P6867)
HBSS 10× (Gibco 14185-045)
HEPES (acid) (Sigma H3375)
Sodium carbonate (Sigma S7795) $Na_2CO_3$
Magnesium sulfate (Sigma M7774) $MgSO_4$
Calcium chloride (Sigma C5080) $CaCl_2$
Black tips (Molecular Devices 9000-0549)
Black 96-well plates (Beckton Dickinson 356640)
DMSO (Sigma D 5879)
1.7. Results The test compounds have an IC50 in the FlipR test of less than 10 000 nM. Some of these compounds have an IC50 in the FlipR test of less than 1000 nM, or even less than 200 nM. By way of example, compounds 1, 2, 4, 5, 7, 9, 11, 13, 18, 20, 24, 26, 29, 33, 36, 42 and 44 of the table have IC50 values of 1600, 1700, 630, 540, 330, 1400, 566, 846, 1080, 116, 102, 170, 253, 450, 450, 95 and 660 nM, respectively.

The compounds according to the invention may thus be used for the preparation of medicaments, in particular medicaments for inhibiting the urotensin II receptors. Thus, according to another of its aspects, a subject of the invention is medicaments comprising a compound of formula (I), or an addition salt thereof with a pharmaceutically acceptable acid of the compound of formula (I), or alternatively an enantiomer, a diastereoisomer or a racemic mixture of this compound.

These medicaments find their use in therapy, especially in the treatment and/or prevention of congestive cardiac insufficiency, cardiac ischemia, myocardial infarction, cardiac hypertrophy and fibrosis, coronary diseases and atherosclerosis, systemic arterial hypertension, pulmonary hypertension, portal hypertension, hepatic fibrosis, post-angioplasty restenosis, renal insufficiency and more particularly acute and chronic renal insufficiency of diabetic and/or hypertensive origin, diabetes, inflammation in general, fibrosis in general and aneurisms.

These medicaments also find their use in therapy, in the treatment and/or prevention of central nervous system disorders, especially including neurodegenerative diseases, strokes, stress, anxiety, aggressiveness, depression, schizophrenia or sleeping disorders.

Medicaments comprising urotensin II-antagonist compounds such as the compounds according to the invention also find their use in therapy, in the treatment and/or prevention of vomiting.

These medicaments also find their use in therapy in the treatment of certain cancers.

These medicaments also find their use in therapy, in the treatment and/or prevention of asthma and respiratory diseases.

It should be noted that the compounds according to the invention bearing a group R3 corresponding to an ester function, after oral absorption, may undergo an enzymatic hydrolysis to release the corresponding acid and may thus be useful as prodrugs.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of said compound, an enantiomer, a diastereoisomer or a racemic mixture of this compound, and also at least one pharmaceutically acceptable excipient.

Said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in unit administration form, as a mixture with standard pharmaceutical excipients, to man and animals for the prophylaxis or treatment of the above disorders or diseases.

The appropriate unit administration forms include oral forms such as tablets, soft or hard gel capsules, powders, granules and oral solutions or suspensions, sublingual, buccal, intratracheal, intraocular, intranasal and inhalation administration forms, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---:|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

According to another of its aspects, the present invention also relates to a method for treating the pathologies indicated above, which comprises the administration to a patient of an effective dose of a compound according to the invention, or a pharmaceutically acceptable salt thereof, or alternatively an enantiomer, a diastereoisomer or a racemic mixture of this compound.

The invention claimed is:
1. A compound corresponding to formula (I)

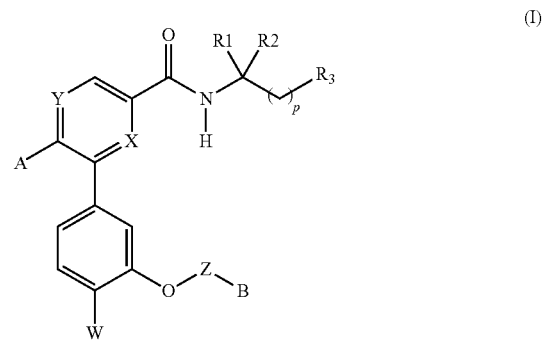

in which:
X is a nitrogen atom and Y is —CR4—, in which R4 represents a hydrogen atom or a (C1-C4) alkyl or alkoxy group;
A represents an unfused aryl group, said unfused aryl group optionally substituted with one or more groups selected from halogen atom, hydroxyl group, (C1-C4) alkyl, (C3-5) cycloalkyl, (C1-C4) alkoxy optionally substituted with a (C1-C4) alkoxy, haloalkyl or haloalkoxy group, and nitrile group;
W represents a halogen atom or a haloalkyl group;
Z represents a (C1-C4) alkylene group optionally substituted with one or more groups selected from halogen atom, (C1-C4) alkyl, hydroxyl, and (C1-C4) alkoxy groups;
B represents a group —NR4R5, in which R4 and R5 represent, independently of each other, a (C1-C4) alkyl group;
either, R1 represents a hydrogen atom and R2 represents a (C1-C4) alkyl group,
or R1 and R2 form, together with the carbon atom to which they are attached, a monocyclic or polycyclic system selected from a (C3-C8) cycloalkyl group, a bridged bicyclic group, and a bridged tetracyclic group, wherein said monocyclic or polycyclic system is optionally substituted with one or more hydroxyl groups;
either R3 represents a group C(O)R5 with R5 representing a (C1-C4) alkoxy group optionally substituted with a (C1-C4) alkoxy group or a group NR6R7, with R6 and R7, independently of each other, representing a hydrogen atom or a (C1-C4) alkyl, (C3-5) cycloalkyl, (C1-C4) alkylsulfonyl or haloalkyl group, or R3 represents a group CH₂XR8 in which:
   X represents an oxygen atom and R8 represents a hydrogen atom or a (C1-C4) alkyl group,
   or X represents an NH group and R8 represents a (C1-C4) alkylcarbonyl, (C1-C4) alkylcarboxyl or (C1-C4) alkylsulfonyl group,
or R3 represents a nitrile group (CN);
p represents an integer equal to 0 or 1,
wherein the compound can be in the form of a base or an addition salt with an acid or a base, and enantiomers and diastereoisomers thereof, including racemic mixtures thereof.

2. The compound of claim 1, wherein:
R4 represents a hydrogen atom;
said unfused aryl group is optionally substituted with one or more groups selected from halogen atom, hydroxyl group, (C1-C4) alkyl, (C3-5) cycloalkyl, and (C1-C4) alkoxy optionally substituted with a (C1-C4) alkoxy, haloalkyl or haloalkoxy group;
W represents a halogen atom;
Z represents a (C1-C4) alkylene group;
either, R1 represents a hydrogen atom and R2 represents a (C1-C4) alkyl group,
or R1 and R2 form, together with the carbon atom to which they are attached, a monocyclic or polycyclic system selected from a (C3-C8) cycloalkyl group and a bridged tetracyclic group, wherein said monocyclic or polycyclic system is optionally substituted with one or more hydroxyl groups.

3. The compound of claim 1 wherein:
R4 represents a hydrogen atom;
said unfused aryl group is optionally substituted with one or more groups selected from halogen atom, (C1-C4) alkyl, (C3-5) cycloalkyl, (C1-C4) alkoxy and haloalkoxy;
W represents a halogen atom;
Z represents a (C1-C4) alkylene group;
either, R1 represents a hydrogen atom and R2 represents a (C1-C4) alkyl group,
or R1 and R2 form, together with the carbon atom to which they are attached, a (C3-C8) cycloalkyl group, optionally substituted with one or more hydroxyl groups, or an adamantyl group;
either R3 represents a group C(O)R5 with R5 representing a (C1-C4) alkoxy group optionally substituted with a (C1-C4) alkoxy group or a group NR6R7 with R6 representing a hydrogen atom and R7 representing a hydrogen atom or a (C1-C4) alkyl, (C3-C5) cycloalkyl, (C1-C4) alkylsulfonyl or haloalkyl group,
or R3 represents a group —CH₂XR8 with X representing an oxygen atom and R8 representing a hydrogen atom or a (C1-C4) alkyl group.

4. A compound of claim 1 selected from:
methyl 1-({[6-{4-chloro-3-[3-(dimethylamino)propoxy]phenyl}-5-(4-hydroxy-2-methylphenyl)pyridin-2-yl]carbonyl}amino)cyclohexanecarboxylate;
methyl 1-({[6-{4-chloro-3-[3-(dimethylamino)propoxy]phenyl}-5-(5-hydroxy-2-methylphenyl)pyridin-2-yl]carbonyl}amino)cyclohexanecarboxylate;
methyl 1-({[6-{4-chloro-3-[3-(dimethylamino)propoxy]phenyl}-5-(2-methyl-phenyl) pyridin-2-yl]carbonyl}amino)cyclohexanecarboxylate;
methyl 1-{[(6-{4-chloro-3-[3-(dimethylamino)propoxy]phenyl}-5-[5-(2-methoxyethoxy)-2-methylphenyl]pyridin-2-yl)carbonyl}amino)cyclohexanecarboxylate;
methyl 1-({[6-{4-chloro-3-[3-(dimethylamino)propoxy]phenyl}-5-(5-cyclopropyl-2-methylphenyl)pyridin-2-yl]carbonyl}amino)cyclohexanecarboxylate;
methyl 1-({[6-{4-chloro-3-[3-(dimethylamino)propoxy]phenyl}-5-(5-isopropoxy-2-methylphenyl)pyridin-2-yl]carbonyl}amino)cyclohexanecarboxylate;
methyl 1-({[6-{4-chloro-3-[3-(dimethylamino)propoxy]phenyl}-5-(2-chloro-5-propoxyphenyl)pyridin-2-yl]carbonyl}amino)cyclohexanecarboxylate;
methyl 1-({[6-{4-chloro-3-[3-(dimethylamino)propoxy]phenyl}-5-(5-ethoxy-2-methylphenyl)pyridin-2-yl]carbonyl}amino)cyclohexanecarboxylate;
methyl 1-({[6-{4-chloro-3-[3-(dimethylamino)propoxy]phenyl}-5-(3-hydroxy-2-methylphenyl)pyridin-2-yl]carbonyl}amino)cyclohexanecarboxylate;
methyl 1-{[(6-{4-chloro-3-[3-(dimethylamino)propoxy]phenyl}-5-[5-(difluoromethoxy)-2-methylphenyl]pyridin-2-yl)carbonyl]amino}cyclohexanecarboxylate;
methyl 1-{[(6-{4-chloro-3-[3-(dimethylamino)propoxy]phenyl}-5-[2-(difluoromethyl)-5-methylphenyl]pyridin-2-yl)carbonyl]amino}cyclohexanecarboxylate;
methyl (3S)-3-({[6-{4-chloro-3-[3-(dimethylamino)propoxy]phenyl}-5-(2-chloro-5-methylphenyl)pyridin-2-yl]carbonyl}amino)-4-methylpentanoate;
methyl (3S)-3-({[6-{4-chloro-3-[3-(dimethylamino)propoxy]phenyl}-5-(2,4-dimethylphenyl)pyridin-2-yl]carbonyl}amino)-4,4-dimethylpentanoate;
methyl 2-({[6-{4-chloro-3-[3-(dimethylamino)propoxy]phenyl}-5-(2-chloro-phenyl) pyridin-2-yl]carbonyl}amino)adamantane-2-carboxylate;
2-methoxyethyl (3S)-3-({[6-{4-chloro-3-[3-(dimethylamino)propoxy]phenyl}-5-(2-methylphenyl)pyridin-2-yl]carbonyl}amino)-4,4-dimethylpentanoate;
methyl (3S)-3-({[6-{4-chloro-3-[3-(dimethylamino)propoxy]phenyl}-5-(2-methylphenyl)pyridin-2-yl]carbonyl}amino)-4,4-dimethylpentanoate;
ethyl (3S)-3-({[6-{4-chloro-3-[3-(dimethylamino)propoxy]phenyl}-5-(2-methylphenyl)pyridin-2-yl]carbonyl}amino)-4,4-dimethylpentanoate;
isopropyl (3S)-3-({[6-}4-chloro-3-[3-(dimethylamino)propoxy]phenyl}-5-(2-methylphenyl)pyridin-2-yl]carbonyl}amino)-4,4-dimethylpentanoate;
methyl (3S)-3-({[6-{4-chloro-3-[3-(dimethylamino)propoxy]phenyl}-5-(2-chlorophenyl)pyridin-2-yl]carbonyl}amino)-4,4-dimethylpentanoate;
N-[(1S)-1-(2-amino-2-oxoethyl)-2,2-dimethylpropyl]-6-{4-chloro-3-[3-(dimethylamino)propoxy]phenyl}-5-(2-methylphenyl)pyridine-2-carboxamide;
6-{4-chloro-3-[3-(dimethylamino)propoxy]phenyl}-N-{(1S)-2,2-dimethyl- 1-[2-(methylamino)-2-oxoethyl]propyl}-5-(2-methylphenyl)pyridine-2-carboxamide;
6-{4-chloro-3-[3-(dimethylamino)propoxy]phenyl}-N-[(1 S)-2,2-dimethyl- 1-{2-[(methylsulfonyl)amino]-2-oxoethyl}propyl]-5-(2-methylphenyppyridine-2-carboxamide;
6-{4-chloro-3-[3-(dimethylamino)propoxy]phenyl}-N-[(1S)-1-{2-[(1,1,1-trifluoroethyl)amino]-2-oxoethyl}-2,2-dimethylpropyl]-5-(2-methylphenyl)pyridine-2-carboxamide;
6-{4-chloro-3-[3-(dimethylamino)propoxy]phenyl}-N-[(1S)-1-{2-[cyclo-propyl (methyl)amino]-2-oxoethyl}-2,2-dimethylpropyl]-5-(2-methylphenyl)pyridine-2-carboxamide;
6-{4-chloro-3-[3-(dimethylamino)propoxy]phenyl}-N-[(1S)-1-(2-hydroxyethyl)-2,2-dimethylpropyl]-5-(2-methylphenyl)pyridine-2-carboxamide;
6-{4-chloro-3-[3-(dimethylamino)propoxy]phenyl}-N-[(1S)- 1(2-methoxyethyl)-2,2-dimethylpropyl]-5-(2-methylphenyl)pyridine-2-carboxamide;

6-{4-chloro-3-[3-(dimethylamino)propoxy]phenyl}-N-[(2S)-1-cyano-3,3-dimethylbutan-2-yl]-5-(2-methylphenyl)pyridine-2-carboxamide;

methyl cis-1-({[6-{4-chloro-3-[3-(dimethylamino)propoxy]phenyl}-5-(2,4-dimethylphenyl)pyridin-2-yl]carbonyl}amino)-4-hydroxycyclohexanecarboxylate;

methyl cis-1-({[6-{4-chloro-3-[3-(dimethylamino)propoxy]phenyl}-5-(2-methyl-phenyl) pyridin-2-yl]carbonyl}amino)-4-hydroxycyclohexanecarboxylate; and methyl cis-1-({[6-{4-chloro-3-[3-(dimethylamino)propoxy]phenyl}-5-(5-ethoxy-2-methylphenyl)pyridin-2-yl]carbonyllamino)-4-hydroxycyclohexanecarboxylate.

5. A process for preparing a compound of formula (I) of claim 1 comprising the step of reacting a compound of formula (II):

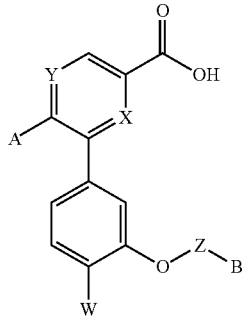

(II)

in which X, Y, Z, W, A and B are as defined in claim 1, with a compound of formula (III):

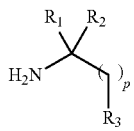

(III)

in which R1, R2, R3, and p are as defined in claim 1.

6. A process for preparing a compound of formula (I) of claim 1 comprising the step of reacting a compound of formula (IV):

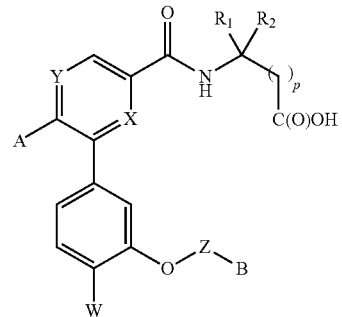

(IV)

in which X, Y, Z, W, A B, R1, R2, and p are as defined in claim 1, with a compound of formula R5H wherein R5 is as defined in claim 1.

7. A process for preparing a compound of formula (I) of claim 1 comprising the step of reacting a compound of formula (IV):

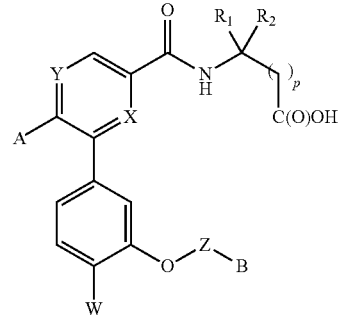

(IV)

in which A, Y, X, R1, R2, p, W, Z and B are as defined in claim 1, with a reducing agent.

8. A medicament comprising a compound of formula (I) as claimed in claim 1, or an addition salt of said compound with a pharmaceutically acceptable acid or base, or alternatively an enantiomer, a diastereoisomer or a racemic mixture of said compound.

9. A pharmaceutical composition comprising a compound of formula (I) as claimed in claim 1, or an addition salt of this compound with a pharmaceutically acceptable acid or base, an enantiomer, a diastereoisomer or a racemic mixture of this compound, and at least one pharmaceutically acceptable excipient.

* * * * *